United States Patent
Drieu et al.

(10) Patent No.: US 7,078,434 B1
(45) Date of Patent: Jul. 18, 2006

(54) USE OF GINKGO EXTRACT

(75) Inventors: Katy Drieu, Paris (FR); Vassilios Papadopoulos, North Potomac, MD (US)

(73) Assignees: Societe de Conseils de Recherches et d'Applications Scientifiques SAS, Paris (FR); Georgetown University, Washington, DC (US)

( * ) Notice: Subject to any disclaimer, the term of this patent is extended or adjusted under 35 U.S.C. 154(b) by 298 days.

(21) Appl. No.: 10/018,448

(22) PCT Filed: Aug. 11, 2000

(86) PCT No.: PCT/US00/22174

§ 371 (c)(1),
(2), (4) Date: Mar. 20, 2002

(87) PCT Pub. No.: WO01/12208

PCT Pub. Date: Feb. 22, 2001

Related U.S. Application Data

(60) Provisional application No. 60/148,604, filed on Aug. 12, 1999.

(51) Int. Cl.
*A61K 31/34* (2006.01)
*A61K 36/16* (2006.01)

(52) U.S. Cl. ............... 514/468; 514/461; 514/473; 424/714

(58) Field of Classification Search ............... 424/714; 514/461, 473
See application file for complete search history.

(56) References Cited

U.S. PATENT DOCUMENTS 4,734,280 A 3/1988 Braquet
5,002,965 A 3/1991 Ramwell
5,346,894 A 9/1994 Korth (Continued)

FOREIGN PATENT DOCUMENTS

DE 38 32 056 3/1990

(Continued)

OTHER PUBLICATIONS

Bernardini, R. et al., "The Alkyl-Ether Phospholipid Platelet-Activating Factor is a Stimulator of the Hypothalamic-Pituitary-Adrenal Axis in the Rat", Endocrinology 125(2):1067-1073 (1989).

(Continued)

*Primary Examiner*—Gollamudi S. Kishore
(74) *Attorney, Agent, or Firm*—Yankwich & Associates; Brian R. Morrill; Alan F. Feeney

(57) ABSTRACT

The present invention is directed to the use of the extract of *Ginkgo biloba* leaves or isolated Ginkgolide B (GKB), a component of the extract of *Ginkgo biloba* leaves in a method for decreasing the expression of peripheral-type benzodiazepine receptor (PBR) in cells of a patient in need thereof. Further, the present invention is directed to the use of the extract of *Ginkgo biloba* leaves or isolated GKB in a method for decreasing the proliferation of cancer cells in a patient. More particularly, the present invention is directed to the use of the extract of *Ginkgo biloba* leaves or isolated GKB in a method of decreasing cancer cell proliferation in a patient wherein the cancer cell is human breast cancer cell. Even more particularly, the present invention is directed to the use of the extract of *Ginkgo biloba* leaves or isolated GKB in method of decreasing cancer cell proliferation in a patient wherein the cancer cell is of the aggressive and invasive phenotype and expresses high levels of PBR in comparison to non-aggressive cancer cell.

14 Claims, 8 Drawing Sheets

U.S. PATENT DOCUMENTS

| | | | |
|---|---|---|---|
| 5,541,183 | A | 7/1996 | Park et al. |
| 6,274,621 | B1 | 8/2001 | Drieu |
| 6,316,690 | B1 * | 11/2001 | Fogarty .......................... 800/3 |
| 2003/0157095 | A1 | 8/2003 | Papdopoulos et al. |

FOREIGN PATENT DOCUMENTS

| | | |
|---|---|---|
| DE | 40 08 868 | 9/1993 |
| DE | 4208868 | 9/1993 |
| EP | 0 359 951 | 3/1990 |
| EP | 0 359 951 B1 | 1/1994 |
| WO | WO 95/18131 | 7/1995 |

OTHER PUBLICATIONS

Blasquez, C. et al., "Effect of Platelet-Activating Factor on Hypothalamic and Hypophyseal Pro-Opiomelanocortin-Related Peptides and Hypothalamo-Pituitary-Adrenal Axis in the Rat", European Journal of Pharmacology, 177:145-153 (1990).

Boralle, N. et al., "Ginkgo Biloba: A Review of its Chemical Composition", Ginkgolides-Chemistry, Biology, Pharmacology and Clinical Perspectives, Edited by P. Braquet, Ph.D., D.Sc., J.R. Prous Science Publishers, S.A., Les Plessis Robinson, France, 1:9-25 (1988).

Bruel, A. et al., "Effects of Ginkgo Biloba Extract on Glucose Transport and Glycogen Synthesis of Cultured Smooth Muscle Cells from Pig Aorta", Pharmacological Res., 21(4):421-429, (1989).

Krieglstein, J., "Neuroprotective Properties of Ginkgo Biloba-Constitutents", Z. Phytother, 15:92-96 (1994).

Oliver, C. et al., "Effect of Ginkgo Biloba Extract on the Hypothalamo-Pituitary-Adrenal Axis and Plasma Catecholamines Levels in Stress", Eur J. Endocrinol., 130(Suppl 2):P3.072 (ABSTRACT) (1994).

Petkov, V.P. et al., "Effects of Standardized Extracts GK501, from Ginkgo Biloba L., G115 from Panax ginseng C.A. Meyer, and their Combination, Gincosan® (PHL-00701), on the Brain Levels of Biogenic Monamines and on the Serum Content of Prolactin, Growth Hormone and ACTH", Phytotherapy Res., 7:139-145 (1993).

Porsolt, R. et al., "Effects of an Extract of Ginkgo Biloba (EGB 761) on "Learned Helplessness" and Other Models of Stress in Rodents", Pharmacology Biochemistry & Behavior, 36:963-971 (1990).

Rapin, J. et al., "Demonstration of the "Anti-Stress" Activity of an Extract of Ginkgo Biloba (EGb 761) Using a Discrimination Learning Task", Gen. Pharmac., 25(5):1009-1016 (1994).

Rapin, J. et al., "Effects of Repeated Treatments With an Extract of Ginkgo Biloba (EGb 761) and Bilobalide on Glucose Uptake and Glycogen Synthesis in Rat Erythrocytes: An Ex Vivo Study", Drug Devel. Res., 31:164-169 (1994).

Rodrigez De Turco, E. et al., "EGb 761 Inhibits Stress-Induced Polydipsia in Rats", Physiology & Behavior, 53:1001-1002 (1993).

Rote Liste (1994), Edited by Cantor. Aulendorf/Wurtt, ECV, Frankfurt, Germany, 94/0112:36001-36012 (1994).

Vasseur, M. et al., "Effects of Repeated Treatments with an Extract of Ginkgo Biloba (EGb 761), Bilobalide and Ginkgolide B . . . ", Gen. Pharmacology, 25(1):31-46 (1994).

Borchers, A. et al., "Mushrooms, tumors and immunity," Proc. Soc. Exp. Biol. Med., 1999, 221:281-93.

Broaddus, W. et al., "Peripheral-type benzodiazepine receptors in human glioblastomas: pharmacologic characterization and photoaffinity labeling of ligand recognition site," Brain Res., 1990, 518:199-208.

Cornu, P. et al., "Increase in ω3 (peripheral-type benzodiazepine) binding site densitites in different types of human brain tumours," Acta Neurochir (Wein), 1992, 119:146-152.

Hardwick, M. et al., "Peripheral-type benzodiazepine receptor (PBR) in human breast cancer: correlation of breast cancer cell aggressive phenotype with PBR expression, nuclear localization, and PBR-mediated cell proliferation and nuclear transport of cholesterol," Cancer Res., 1999, 59:831-842.

Hauns, B. et al., "Phase II study with 5-flourouracil and ginkgo biloba extract (GBE 761 ONC) in patients with pancreatic cancer," Arzneimittelforschung, 1999, 49:1030-1034.

Hu, K. et al., "Antineoplastic agents; I. Three spirostanol glycosides from rhizomes of Dioscorea collettii var. hypoglauca," Planta Med., 1996, 62:573-5.

Huang, Y. et al., "Antitumor effects and pharmacological interaction of xiao-chai-hu-tang (sho-saiko-to) and interleukin 2 in murine renal cell carcinoma," Keio J Med., 1997, 46:132-7.

Ito, H. et al., "Effects of a blended Chinese medicine, xaio-chai-hu-tang, on Lewis lung carcinoma growth and inhibition of lung metastasis, with special reference to macrophage activation," Jpn. J. Pharmacol., 1986, 41:307-14.

Kato, M. et al., "The herbal medicine Sho-saiko-to inhibits growth and metastasis of malignant melanoma primarily developed in ret-transgenic mice," J. Invest. Dermatol., 1998, 111:640-4.

Katz, Y. et al., "Dramatic increase in peripheral benzodiazepine binding sites in human colonic adenocarcinoma as compared to normal colon," Eu. J. Pharm., 1988, 148:483-484.

Katz, Y. et al., "Increased density of peripheral benzodiazepine-binding sites in ovarian carcinomas as compared with benign ovarian tumours and normal ovaries," Clinical Science, 1990, 78:155-158.

Michaud, D. et al., "Fruit and vegetable intake and incidence of bladder cancer in a male prospective cohort," J. Natl. Cancer Inst., 1999, 91:605-13.

Miettinen, H. et al., "Expression of peripheral-type benzodiazepine receptor and diazepam binding inhibitor in human astrocytomas: relationship to cell proliferation," Cancer Res., 1995, 55:2691-2695.

Monte, M. et al., "Inhibition of lymphocyte-induced angiogenesis by free radical scavengers," Free Radic. Biol. Med., 1994:259-266.

Moyad, M. et al., "Traditional Chinese medicine, acupuncture, and other alternative medicines for prostate cancer: an introduction and the need for more research," Semin. Urol. Oncol., 1999, 17:103-110.

Nakahata, N. et al., "Analysis of inhibitory effects of scutellariae radix and baicalein on postaglandin E2 production in rat C6 glioma cells," Am. J. Chin. Med., 1998, 26:311-23.

Pappata, S. et. al., "PET study of carbon-11-PK 11195 binding to peripheral-type benzodiazepine sties in glioblastoma: a case report," J. Nuclear Med., 1991, 32:1608-1610.

Sakamoto, S. et al., "Effects of Chinese herbal medicines on DNA-synthesizing enzyme activities in mammary tumors of mice," Am. J. Chin. Med., 1994, 22:43-50.

Sasaki, T. et al., "Effects of isothiocyanates on growth and metastaticity of B16-F10 melanoma cells," Nutr. Cancer, 1999, 33:76-81.

Sengupta, A. et al., "The anti-carcinogenic role of lycopene, abundantly present in tomato," Eur. J. Cancer Prev., 1999, 8:325-30.

Yamashiki, M. et al., "Herbal medicine 'Sho-saiko-to' induces tumour necrosis factor-alpha and granulocyte colony-stimulating factor in vitro in peripheral blood mononuclear cells of patents with hepatocellular carcinoma," J. Gastroenterol. Hepatol., 1996, 11:137-42.

Zheng, Y. et al., "In vitro immunotoxicity and cytotoxicity of trochosanthin against human normal immunocytes and leukemia-lymphoma cells," Immunopharmacol. Immunotoxicol., 1995, 17:69-79.

Zheng, S. et al., "Initial study on naturally occurring products from traditional Chinese hers and vegetables for chemoprevention," J. Cell. Biochem. Suppl., 1997, 27:106-12.

Defeudis, F. V., "Ginkgo biloba extract (EGb 761): Pharmacological activities and clinical applications" 1991, Elsevier, Paris, p. 9-24.

Defeudis, F. V., "Ginkgo biloba extract (EGb 761): From chemistry to the clinic" 1998, Ullstein Medical, p. 7-15.

Ye et al., "Epidemiological and biological evidence for protective effect of ginkgo biloba on ovarian cancer," 2005, 96th Annual Meeting of the American Association for Cancer Research, Apr. 16-29, Anaheim/Orange County, CA, Abstract #3484.

Ye et al., "Ginkgo biloba and ginkgolides as potential agents for ovarian cancer prevention," 2005, Frontiers in Cancer Prevention Research Meeting, Oct. 30-Nov. 2, Baltimore, MD, Abstract #A100.

"Gingko may prevent ovarian cancer," Brigham and Women's Hospital Press Release, Oct. 31, 2005.

* cited by examiner

USE OF GINKGO EXTRACT

This application claims the benefit of 60/148,604 filed Aug. 12, 1999.

BACKGROUND OF THE INVENTION

The present invention is directed to the use of the extract of *Ginkgo biloba* leaves or isolated ginkgolide B (GKB), a component of the extract of *Ginkgo biloba* leaves in a method for decreasing the expression of peripheral-type benzodiazepine receptor (PBR) in cells of a patient in need thereof. Further, the present invention is directed to the use of the extract of *Ginkgo biloba* leaves or isolated GKB in a method for decreasing the proliferation of cancer cells in a patient in need thereof. More particularly, the present invention is directed to the use of the extract of *Ginkgo biloba* leaves or isolated GKB in a method of decreasing cancer cell proliferation in a patient in need thereof wherein said cancer cell is human breast cancer cells. Even more particularly, the present invention is directed to the use of the extract of *Ginkgo biloba* leaves or isolated GKB in a method of decreasing cancer cell proliferation in a patient in need thereof wherein said cancer cell are of the aggressive and invasive phenotype and expresses high levels of PBR in comparison to non-aggressive cancer cells.

In another aspect, the present invention is directed to the use of extract of *Ginkgo biloba* leaves to decrease the expression of thirty-five (35) gene products as is further detailed, hereinbelow.

It is preferred that a particular formulation of *Ginkgo biloba* leaves extract known as EGB 761® (a product of IPSEN, Paris, France) be a constituent in a composition or used in a method of the present invention.

*Ginkgo biloba* is one of the most ancient trees and extracts from its leaves have been used in traditional medicine for several hundred years. There are numerous studies describing the beneficial effects of *Ginkgo biloba* extracts on patients with disturbances in vigilance, memory, and cognitive functions associated with aging and senility, and on those with all types of dementias, mood changes, and the ability to cope with daily stressors. A standardized extract of *Ginkgo biloba* leaves, termed EGB 761®, has been used in most of these studies. This extract is also known to have cardioprotective effects (DeFeudis F. V. *Ginkgo biloba* extract (EGB 761®): from chemistry to clinic. Ullstein Medical, Wisbaden, Germany. 400 pp. 1998; Tosaki, A., Droy-Lefaix, M. T., Pali, T., and Das, D. K., Free Rad. Biol. Med., 14: 361–370, 1993). These effects have been attributed, at least in part, to the free radical scavenging properties of EGb761®, probably due to the presence of flavonoid or terpenoid constituents in the extract. Recent in vivo and in vitro studies demonstrated that the terpene constituents of EGB 761®, ginkgolides and bilobalide, have anti-oxidant properties (Pietri, S., Maurelli, E., Drieu, K., and Culcasi, M., J. Mol. Cell. Cardiol., 29: 733–742, 1997; Yao, Z., Boujrad, N., Drieu, K., and Papadopoulos, V., Adv. *Ginkgo Biloba* Res. 7: 129–138, 1998). Other studies of EGB 761® have reported medicinal value of the product in the treatment of a variety of clinical disorders including cerebrovascular and peripheral vascular insufficiencies associated with aging and senility. See e.g., *Ginkgo biloba* Extract (EGB 761®) Pharmacological Activities and Clinical Applications, DeFeudis, F. V., Eds, Elsevier, 1991; and Ullstein Medical 1998, *Ginkgo biloba* extract (EGB 761®), Eds. Wiesbaden, DeFeudis, F. V. The extract contains 24% ginkgo-flavone glycosides, 6% terpene lactones (ginkgolides and bilobalide), about 7% proanthocyanidins and several other constituents. See Boralle, N., et al., In: Ginkgolides, Chemistry, Biology, Pharmacology and Clinical perspectives, Ed: Braquet, P., J. R. Prous Science Publishers, 1988.

Tumor progression is a multi-step process in which normal cells gradually acquire more malignant phenotypes, including the ability to invade tissues and form metastases, the primary cause of mortality in breast cancer. During this process, the "aberrant" expression of a number of gene products may be the cause or the result of tumorigenesis. Considering that the first step of tumor progression is cell proliferation, it can be proposed that tumorigenesis and malignancy are related to the proliferative potential of tumoral cells.

Studies in a number of tumors such as rat brain containing glioma tumors (Richfield, E. K. et al. (1988) *Neurology* 38:1255–1262), colonic adenocarcinoma and ovarian carcinoma (Katz, Y. et al. (1988) *Eur. J. Pharmacol.* 148:483–484 and Katz, Y. et al. (1990) *Clinical Sci.* 78:155–158) have shown an abundance of peripheral-type benzodiazepine receptors (PBR) compared to normal tissue. Moreover, a 12-fold increase in PBR density relative to normal parenchyma, was found in human brain glioma or astrocytoma (Cornu, P. et al. (1992) *Acta Neurochir.* 199:146–152). The authors suggested that PBR densities may reflect the proliferative activity of the receptor in these tissues. Recently, the involvement of PBR in cell proliferation was further shown (Neary, J. T. et al. (1995) Brain Research 675:27–30; Miettinen, H. et al. (1995) *Cancer Research* 55:2691–2695), and its expression of human astrocytic tumors was found to be associated with tumor malignancy and proliferative index (Miettinen, H. et al. supra; Alho, H. (1994) *Cell Growth Different.* 5:1005–1014). Further studies have shown that PBR receptors are abundant in human glioblastomas (Broaddus, W. C., et al., *Brain Research*, Vol. 518:199–208, 1990; and Pappata, S., et al., *J. Nuclear Med.*, 32:1608–1610, 1991).

PBR is an 18-kDa protein discovered as a class of binding sites for benzodiazepines distinct from the GABA neurotransmitter receptor (Papadopoulos, V. (1993) *Endocr. Rev.* 14:222–240). PBR are extremely abundant in steroidogenic cells and found primarily on outer mitochondrial membranes (Anholt, R. et al. (1986) *J. Biol. Chem.* 261: 576–583). PBR is thought to be part of the multimeric complex composed of the 18-kDa isoquinoline-binding protein and the 34-kDa pore-forming voltage-dependent anion channel protein, preferentially located on the outer/inner mitochondrial membrane contact sites (McEnery, M. W. et al. *Proc. Natl. Acad. Sci.* U.S.A. 89:3170–3174; Garnier, M. et al. (1994) *Mol. Pharmacol.* 45:201–211; Papadopoulos, V. et al. (1994) *Mol. Cel. Endocr.* 104:R5–R9). Drug ligands of PBR, upon binding to the receptor, stimulate steroid synthesis in steroidogenic cells in vitro (Papadopoulos, V. et al. (1990) *J. Biol. Chem.* 265:3772–3779; Ritta, M. N. et al. (1989) Neuroendocrinology 49:262–266; Barnea, E. R. et al. (1989) *Mol. Cell Endocr.* 64:155–159; Amsterdam, A. and Suh, B. S. (1991) *Endocrinology* 128:503–510; Yanagibashi, K. et al. (1989) *J. Biochem.* (Tokyo) 106: 1026–1029). Likewise, in vivo studies showed that high affinity PBR ligands increase steroid plasma levels in hypophysectomized rats (Papadopoulos V. et al (1997) *Steroids* 62:21–28). Further in vitro studies on isolated mitochondria provided evidence that PBR ligands, drug ligands, or the endogenous PBR ligand, the polypeptide diazepam binding inhibitor (BDI) (Papadopoulos, V. et al. (1997) *Steroids* 62:21–28), stimulate pregnenolone formation by increasing the rate of cholesterol transfer from the outer to the inner mitochondrial membrane (Krueger, K. E. and Papadopoulos, V. (1990) *J. Biol. Chem* 265:15015–15022; Yanagibashi, K. et al. (1988) *Endocrinology* 123: 2075–2082; Besman, M. J. et al. (1989) *Proc. Natl. Acad. Sci. U.S.A.* 86:4897–4901; Papadopoulos, V. et al. (1991) *Endocrinology* 129:1481–1488).

Based on the amino acid sequence of the 18-kDa PBR, a three dimensional model was developed (Papadopoulos, V. (1996) In: The Leydig Cell. Payne, A. H. et al. (eds) Cache River Press, IL, pp. 596–628). This model was shown to accomodate a cholesterol molecule and function as a channel, supporting the role of PBR in cholesterol transport. Recently we demonstrated the role of PBR in steroidogenesis by generating PBR negative cells by homologous recombination (Papadopoulos, V. et al. (1997) *J. Biol. Chem.* 272:32129–32135) that failed to produce steroids. However, addition of the hydrosoluble analogue of cholesterol, 22R-hydroxycholesterol, recovered steroid production by these cells, indicating that the cholesterol transport mechanism was impaired. Further cholesterol transport experiments in bacteria expressing the 18-kDa PBR protein provided definitive evidence for a function as a cholesterol channel/transporter (Li and Papadopoulos, V. et al., (1998) Endocrinology).

We hypothesized that the peripheral-type benzodiazepine receptor is part of the changes in cellular and molecular functions that account for the increased aggressive behavior in cancer, and we chose to examine this hypothesis in human breast cancer. Breast cancer is the most common neoplasm and the leading cause of cancer-related deaths for women in most developing countries (Lippman, M. E. (1993) *Science* 259:631–632), affecting nearly 184,000 women, with over 46,000 deaths annually in the U.S. alone (American Cancer Society, 1996). Human breast cells are unlike brain and gonadal cells and cannot produce steroids, but like many other cells in the body, are able to metabolize steroids.

Increased PBR expression correlates with increased aggressive behavior of tumor cells. Invasive tumors invade and grow locally but they do not metastasize. However, the aggressive tumors have the ability to invade and metastasize through the blood vessels to different places of the human body. Tumor metastasis into vital organs (such as lungs) is the most common cause of death.

The correlation between high levels of expression of PBR and metastatic potential in for human breast cancer is shown in copending U.S. application Ser. No. 09/047,652 filed Mar. 25, 1998, in which Vassilios Papadopoulos of the instant application is a co-inventor. However, due to the involvement of PBR in cell proliferation, and the expression of PBR in all cells, it is likely that this correlation would exist for other solid tumors and cancers such as prostate cancer, colon cancer, brain tumors, and tumors in steroid producing tissues such as gonadal tumors, to name a few.

SUMMARY OF THE INVENTION

In one aspect, the present invention is directed to a method of combating cancer in a patient in need of such combating, wherein the cancer is caused by the deregulation of expression of proteins having a role in regulating tumor cells, which comprises administering an effective amount of *Ginkgo biloba* extracts or isolated Ginkgolide B to said patient.

In another aspect, the present invention is directed to a method of combating the proliferation of cancer cells in a patient in need of such combating, wherein the proliferation is caused by the deregulation of expression of proteins having a role in regulating tumor cells, which comprises administering an effective amount of *Ginkgo biloba* extracts or isolated Ginkgolide B to said patient.

In another aspect, the present invention is directed to a method of combating the proliferation of cancer cells in a patient in need of such combating, wherein the proliferation is caused by over-expression of proteins having a role in regulating tumor cells, which comprises administering an effective amount of *Ginkgo biloba* extracts or isolated Ginkgolide B to said patient.

In another aspect, the present invention is directed to a method of combating the proliferation of cancer cells having an aggressive phenotype in a patient in need of such combating, wherein the proliferation is caused by the over-expression of peripheral-type benzodiazepine receptor protein, which comprises administering an effective amount of *Ginkgo biloba* extracts or isolated Ginkgolide B to said patient.

In another aspect, the present invention is directed to a method of combating the proliferation of cancer cells, where the proliferation is caused by the over-expression of oncogenes, by decreasing the expression of said oncogenes in a patient in need of such combating, which comprises administering an effective amount of *Ginkgo biloba* extracts or isolated Ginkgolide B to said patient. A preferred method of the immediately foregoing method is where said oncogenes are one or more of APC, PE-1, RhoA and c-Jun.

In another aspect, the present invention is directed to a method of decreasing the expression of peripheral-type benzodiazepine receptor in cancer cells in a patient in need of such decreasing, wherein said cancer cells express an abnormal level of peripheral-type benzodiazepine receptor relative to normal cancer cells, which comprises administering an effective amount of *Ginkgo biloba* extracts or isolated Ginkgolide B to said patient. A preferred method of the immediately foregoing method is where the cancer cells are human breast cancer cells; human glioblastomas; human brain tumors; human astrocytomas; human colonic carcinoma; human colonic adenocarcinoma; human ovarian carcinomas; and human hepatocellular carcinoma.

In another aspect, the present invention is directed to a method of decreasing the expression of peripheral-type benzodiazepine receptor mRNA in cancer cells in a patient in need of such decreasing, which comprises administering an effective amount of *Ginkgo biloba* extracts or isolated Ginkgolide B to said patient.

In another aspect, the present invention is directed to a method of increasing the expression of c-Myc protooncogene in a patient in need of such increasing, which comprises administering an effective amount of *Ginkgo biloba* extracts or isolated Ginkgolide B to said patient.

In another aspect, the present invention is directed to a method of decreasing the expression of cell cycle regulators prothymosin-$\alpha$, CDK2, p55CDC, myeloblastin and p120 proliferating-cell nuclear antigen (PCNA) in a patient in need of such decreasing, which comprises administering an effective amount of *Ginkgo biloba* extracts or isolated Ginkgolide B to said patient.

In another aspect, the present invention is directed to a method of decreasing the expression of intracellular signal transduction modulators NET1 and ERK2, in a patient in need of such decreasing, which comprises administering an effective amount of *Ginkgo biloba* extracts or isolated Ginkgolide B to said patient.

In another aspect, the present invention is directed to a method of decreasing the expression of apoptosis-related proteins Adenosine A2A Receptor, Flt3 ligand, Grb2, Clusterin, RXR-β, Glutathione S-transferase P, N-Myc, TRADD, SGP-2 and NIP-1, in a patient in need of such decreasing, which comprises administering an effective amount of *Ginkgo biloba* extracts or isolated Ginkgolide B to said patient.

In another aspect, the present invention is directed to a method of decreasing the expression of transcription factors Id-2, ATF-4, ETR101 and ETR-103 in a patient in need of such decreasing, which comprises administering an effective amount of *Ginkgo biloba* extracts or isolated Ginkgolide B to said patient.

In another aspect, the present invention is directed to a method of decreasing the expression of growth factors macrophage colony-stimulating factor-1, heparin-binding EGF-like growth factor, hepatocyte growth factor-like protein and inhibin α, in a patient in need of such decreasing, which comprises administering an effective amount of *Ginkgo biloba* extracts or isolated Ginkgolide B to said patient.

In another aspect, the present invention is directed to a method of decreasing the expression of cell adhesion molecules CD19 B-lymphocyte antigen, L1CAM, β-catenin, integrin subunits α3, α4, α6, β5, and αM, in a patient in need of such decreasing, which comprises administering an effective amount of *Ginkgo biloba* extracts or isolated Ginkgolide B to said patient.

In another aspect, the present invention is directed to a method of decreasing the expression of genes APC, PE-1, RhoA, c-Jun, prothymosin-α, CDK2, p55CDC, myeloblastin, p120 proliferating-cell nuclear antigen (PCNA), NET1, ERK2, Adenosine A2A Receptor, Flt3 ligand, Grb2, Clusterin, RXR-β, Glutathione S-transferase P, N-Myc, TRADD, SGP-2, NIP-1, Id-2, ATF-4, ETR-101, ETR-103, macrophage colony-stimulating factor-1, heparin-binding EGF-like growth factor, hepatocyte growth factor-like protein, inhibin α, CD19 B-lymphocyte antigen, L1CAM, β-catenin, and integrin subunits α3, α4, α6, β5, and αM, in a patient in need of such decreasing, which comprises administering an effective amount of *Ginkgo biloba* extracts or isolated Ginkgolide B to said patient.

In another aspect, the present invention is directed to a pharmaceutical composition comprising an effective amount of *Ginkgo biloba* extracts or isolated Ginkgolide B for combating cancer and a pharmaceutically acceptable carrier or diluent.

Of all of the foregoing methods and compositions of the present invention, a preferred embodiment of each is where the *Ginkgo biloba* extracts is EGB 761®.

Further, of all the foregoing methods and compositions of the present invention, it is preferred that Ginkgolide B is used.

BRIEF DESCRIPTION OF THE DRAWINGS

The file of this patent contains at least one drawing executed in color (FIG. 11). This photograph is retained by the International Bureau as part of the record copy.

DETAILED DESCRIPTION

Figure 1:
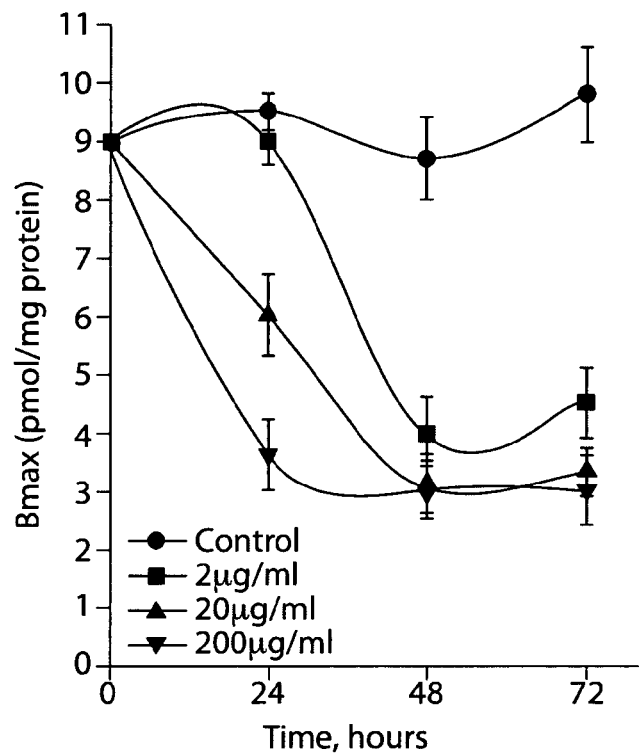
FIG. 1. Effect of various concentrations of EGB 761® on MDA-231 PBR ligand binding capacity. MDA-231 cells were cultured as described under Materials and Methods. Cells were treated with the indicated concentrations of the injectable form of EGB 761®. At the indicated time periods cells were collected and PBR ligand binding characteristics were determined by Scatchard analysis. Data points represent the mean±S.D. of three independent experiments carried out in triplicate.

The term "*ginkgo* terpenoid" includes all of the naturally occurring terpenes which are derived from the gymnosperms tree *Ginkgo biloba* as well as synthetically produced *ginkgo* terpenoids and pharmaceutically active derivatives and salts thereof and mixtures thereof. Examples of *ginkgo* terpenoids include ginkgolides. Examples of *ginkgo* terpenoids are disclosed in Ginkgolides, Chemistry, Biology, Pharmacology, and Clinical Perspectives, J. R. Provs. Science Publishers, Edited by P. Braguet (1988); F. V. DeFeudis, *Ginkgo Biloba* Extract (EGB 761®); Pharmacological Activities and Clinical Applications, Elsevier, Chapter II (1991).

The term "ginkgolide" as used herein include the various ginkgolides disclosed in the books cited above as well as non-toxic pharmaceutically active derivatives thereof. Examples of ginkgolide derivatives include tetrahydro derivatives, acetyl derivatives, and alkyl esters such as the monoacetate derivatives and triacetate derivatives disclosed in Okabe, et al., J. Chem. Soc. (c), pp. 2201–2206 (1967). Ginkgolide B has the following structure and as used herein, refers to isolated ginkgolide B:

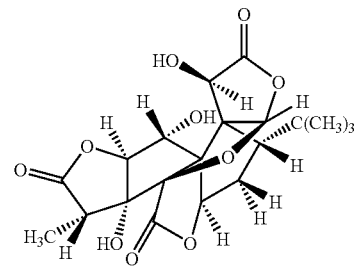

The term "*Ginkgo biloba* extract" as used herein includes a collection of natural molecules, including terpenoids, derived from the leaves of the *Ginkgo biloba* tree. Preferably, the extract is the specific formulation of *Ginkgo biloba* extract known as EGB 761®.

The term "combating" as used herein means preventing, inhibiting and or decreasing whatever the word "combating" acts upon, e.g., combating cancer cell proliferation means that the cancers cells are prevented and inhibited from proliferating further and or the degree or rate of proliferation is decreased.

The level of expression of PBR, for the purposes of diagnosis or prognosis of a cancer or tumor, can be detected at several levels. Using standard methodology well known in the art, assays for the detection and quantitation of PBR RNA can be designed, and include northern hybridization assays, in situ hybridization assays, and PCR assays, among others. See e.g., Maniatis, Fitsch and Sambrook, Molecular Cloning; A Laboratory Manual (1982) or DNA Cloning, Volumes I and II (D. N. Glover ed. 1985), or Current Protocols in Molecular Biology, Ausubel, F. M. et al. (Eds), Wiley & Sons, Inc. for the general description of methods for nucleic acid hybridization. Polynucleotide probes for the detection of PBR RNA can be designed from the sequence available at accession number L21950 for the human PBR sequence (Riond, J. et al. (1991) *Eur. J. Biochem.* 195: 305–311; Chang, Y. J. et al. (1992) *DNA and Cell Biol.* 11:471–480). The sequence of PBR from other sources such as bovine (Parola, A. L. et al. (1991) *J. Biol. Chem* 266: 14082–14087) and mouse (Garnier, M. et al. (1994) *Mol Phar.* 45:201–211) are also known.

The complete sequence of the PBR, normal or mutant, can be used for a probe to detect RNA expression. Alternatively, a portion or portions of the sequence can be used. Methods for designing probes are known in the art. Polynucleotide sequences are preferably homologous to or complementary to a region of the PBR gene, preferably, the sequence of the region from which the polynucleotide is derive is homologous to or complementary to a sequence which is unique to the PBR gene. Whether or not a sequence is unique to the PBR gene can be determined by techniques known to those of skill in the art. For example, the sequence can be compared to sequences in databanks, e.g., GenBank. Regions from which typical DNA sequences may be derived include but are not limited to, for example, regions encoding specific epitopes, as well as non-transcribed and/or non-translated regions.

PBR ligands or anti-PBR antibodies, or fragments of ligand and antibodies capable of detecting PBR may be labeled using any of a variety of labels and methods of labeling for use in diagnosis and prognosis of disease, such as breast cancer, particularly for assays such as Positron Emission Tomography and magnetic resonance imaging (Leong, D. et al. (1996) *Alcohol Clin. Exp. Res.* 20: 601–605). Examples of types of labels which can be used invention include but are not limited to enzyme labels, radioisotopic labels, non-radioactive isotopic labels and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate insomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{32}$P, $^{35}$S, 14C, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, $^{11}$C, $^{19}$F, 123I, etc.

Examples of suitable non-radioactive isotopic labels include $^{157}$Gd, $^{55}$Mn, $^{162}$Dy, $^{52}$Tr, $^{46}$Fe, etc.

Examples of suitable fluorescent labels include a $^{152}$Eu label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, etc.

We examined herein the effect of *Ginkgo biloba* extracts, more specifically EGB 761® and GKB on PBR expression and cell proliferation, particularly in human breast cancer cells. We used the highly aggressive cell line MDA-231, which expresses over 60-fold higher levels of PBR ligand binding and mRNA relative to the non-aggressive cell line MCF-7. EGB 761® and GKB decreased in a time- and dose-dependent manner PBR expression and cell proliferation in MDA-231 cells whereas EGB 761® and GKB did not affect the MCF-7 cell proliferation to the same degree. This effect was reversible and it was not due to the antioxidant properties of the compounds tested.

The determination of elevated levels of PBR is done relative to a sample with no detectable tumor. This may be from the same patient or a different patient. For example, a first sample may be collected immediately following surgical removal of a solid tumor. Subsequent samples may be taken to monitor recurrence of tumor growth and/or tumor cell proliferation. Additionally, other standards may include cells of varying aggressive phenotype such that an increase or decrease in aggressive phenotype can be accessed.

The distinct sub-cellular localization of PBR in the cytoplasm of epithelial cells of normal breast ducts and the absence of staining in the nucleus and the perinuclear area of the aggressive tumor cells provides a simple method for diagnosing the aggressive phenotype of a tumor cell. Immunostaining using labeled PBR ligand or labeled PBR antibody or fragment of ligand or antibody capable of binding to PBR and determining the sub-cellular location of PBR in the cellular samples provides yet another diagnostic assay of the present invention. In addition, antiserum which recognizes PBR can also be used along with a secondary antibody reactive with the primary antibody. Immunostaining assays are well known in the art, and are additionally described in the Examples below with respect to breast cancer cells and biopsies.

An increase in the level of PBR is determined when the level of PBR in a tumor cell is about 2–3 times the level of PBR in the normal cell, up to about 10–100 times the amount of PBR in a normal cell.

Cell Culture and Treatments. Human breast cancer cell lines (MCF-7 and MDA-231) were obtained from the Lombardi Cancer Center, Georgetown University Medical Center. Cell lines were cultured on polystyrene culture dishes (Corning) and grown in Dulbecco's modified Eagle medium (DMEM) supplemented with 10% fetal bovine serum (FBS). The injectable form (IPS200) of the standardized *Ginkgo biloba* extract EGB 761® was used. This injectable form is devoid of protocyanidins, which are known to interact with proteins in vitro (Defeuder, 1998 Ullstein Medical). The injectable form of EGB 761® and GKB (BN 52021) isolated from EGB 761® were provided by the Institut Henri Beaufour-IPSEN (Paris, France).

Radioligand Binding Assays. Cells were scraped from 150 mm culture dishes into 5 ml phosphate buffered saline (PBS), dispersed by trituration, and centrifuged at 500×g for 15 min. Cell pellets were re-suspended in PBS and assayed for protein concentration. [$^3$H]PK 11195 binding studies on 50 μg of protein from cell suspensions were performed as previously described (Papadopoulos, V. et al., 1990, J. Biol. Chem. 265: 3772–3779; Hardwick, M. et al., 1999, Cancer Research, 59: 631–632) the contents of which are incorporated herein by reference. [N-methyl-3H]PK 11195 (1-(2-chlorophenyl)-N-methyl-N-(1-methyl-propyl)-3-isoquinolinecarboxamide; sp. Act. 83.50 (Ci/mmol), was obtained from Du Pont-New England Nuclear (Wilmington, Del.) and PK 11195 was obtained from Research Biochemicals Incorporated (Natick, Mass.). Scatchard plots were analyzed by the LIGAND program (Munson, P J, and Robbard, D. 1980, Anal. Biochem., 107: 220–239) (BIOSOFT, Ferguson, Mo.).

Protein Measurement. Protein levels were measured by the Bradford method (Bradford, M M, 1976, Anal. Biochem., 72: 248–254) using the Bio-Rad Protein Assay kit (Bio-Rad Laboratories, Hercules, Calif.) with bovine serum albumin as a standard.

RNA (Northern) Analysis. PBR mRNA expression in MDA-231 cells treated with the various compounds was examined by Northern Blot analysis as we previously described (Hardwick, M., et al., 1999, Cancer Research, 59: 831–842). In brief, total cellular RNA was isolated using the RNAzol B reagent (TEL-TEST, Inc., Friendswood, Tex.) and chloroform. 20 μg of total RNA from each cell line were run on 1% agarose gels and transferred overnight to nylon membranes (S&S Nytran, Schleicher & Schuell, Keene, N. H.) (21). A 0.2 kb human PBR (hPBR) cDNA fragment (derived from the pCMV5-PBR plasmid vector containing the full length hPBR kindly given by Dr. Jerome Strauss, University of Pennsylvania, PA) was radiolabeled with [α-$^{32}$P]dCTP using a random primers DNA labeling system (Life Technologies, Gaithersburg, Md.). The hybridization conditions were as we previously described (Hardwick, M., et al., 1999, Cancer Research, 59: 831–842). Autoradiography was performed by exposing the blots to X-OMAT AR film (Kodak, Rochester, N.Y.) at −70° C. for 4–48 hr. Quantification of PBR mRNA was carried out using the SigmaGel software (Jandel Scientific, San Rafael, Calif.).

Nucleic Acid Arrays. We used the Atlas human cDNA expression array I from Clontech (Palo Alto, Calif.). This array contains 588 human PCR-amplified cDNA fragments of 200–500 bp long immobilized on a positively charged nylon membrane. MDA-231 cells were treated with and without 20 µl/ml EGB 761® for 48 hours. Poly A+ RNA was isolated from control and EGB 761®-treated cells. $^{32}$P-labeled cDNA probes were generated from each poly A+ RNA and hybridized to the Atlas array according to the manufacturer's recommendations. Autoradiography was performed by exposing the blots to X-OMAT AR film (Kodak, Rochester, N.Y.) at −70° C. for 4–96 hr. Quantification of the hybridization seen was carried out using the SigmaGel software (Jandel Scientific, San Rafael, Calif.). Multiple exposures were used in order to detect genes expressed at low levels. The three internal controls, ubiquitin, G3PDH and β-actin were used to compare the relative expression levels of the detected gene products in the control and EGB 761®-treated cells. Experimental variations were corrected using the ratios of gene expression versus the internal controls. The effect of the EGB 761® treatment on each gene product is expressed as % of control (untreated) cells. The results presented herein show genes affected consistently, at a level above 30% of control, by the EGB 761® treatment.

BrdU Cell Proliferation Assays. MDA-231 cells were plated on 96-well plates (Corning, Corning, N.J.) at a concentration of approximately 10,000 cells/well (24 h incubation) or approximately 5,000 cells/well (48 h incubation) in DMEM supplemented with 0.1% FBS. The cells were then incubated in 10% FBS with various concentrations of EGB 761® or GKB for the indicated time periods. Differences in cell proliferation were analyzed by measuring the amount of 5-bromo-2'deoxyuridine (BrdU) incorporation determined by the BrdU ELISA (Boehringer Mannheim, Indianapolis, Ind.). Incorporation of BrdU was measured at 450 nm (reference at 690 nm).

Analysis of oxidative stress. Levels of cellular oxidative stress were measured using the fluorescent probe 2,7-dichlorofluorescin diacetate (2,7-DCF; Molecular Probes, Inc., Eugene, Oreg.) as described in Goodman, Y. and Mattson, M. P., Exp. Neurol., 128: 1–12, 1994. In brief, cells were cultured in 96-well plates and treated for 48 hours with the indicated concentrations of EGB 761®. At the end of the treatment the cells were washed and incubated in the presence of 50 µM 2,7-DCF in PBS. Fluorescence was then quantified using the Victor$^2$ quantitative detection fluorometer (EGG-Wallac, Inc., Gaithersburg, Md.).

Biological Evaluation In Vivo. The MDA-231 human breast cancer (estrogen insensitive) xenograft model was used for in vivo screening of EGB 761® and GKB. Based on the in vitro data and previously published in vivo data (23) the doses used were 50 mg/kg for the EGB 761® and 1 mg/kg for the GKB. Female athymic nude mice (NCI/Charles River, Frederick, Md.) are injected subcutaneously with 8×10$^6$ MDA-231 tumor cells and tumors are allowed to form to a volume of ~100 to 150 mm$^3$. At this time, groups of 10 animals per compound were injected either orally for the EGB 761® or intraperitoneally for the GKB once a day for a month. Twice weekly tumor sizes and body weights were recorded for all animals for the 30 days of treatment as well for 30 days after the end of the treatment. At that time the animals were sacrificed and the tumors were removed and processed for immunohistochemistry. Animal care was in accordance with institutional guidelines.

Immunocytochemistry of MDA-231 tumors. MDA-231 tumors removed from the mice treated with or without EGB 761® or GKB were fixed in 10% buffered formalin. Tumors were sectioned and then placed on glass slides and processed as we previously described (19). For immunohistochemistry with anti-PBR primary antibodies, tissue sections were treated with a 30% $H_2O_2$/methanol mixture (1:9 ratio) for 5 min at room temperature to neutralize endogenous peroxidase activity and then washed well with PBS. Primary antibody in 10% calf serum in PBS was added to sections at a concentration of 1:500 at RT for 1 h. Secondary antibody reactions were performed using horseradish peroxidase-coupled goat anti-rabbit secondary antibody diluted 1:500 in PBS supplemented with 10% calf serum. After washing the slides three times in PBS for 2 min each, fresh $H_2O_2$ diluted 1:1,000 with 3-amino-9-ethyl carbazole (AEC) was added and slides were incubated for 1 h at 37° C. The slides were then rinsed in distilled $H_2O$ before mounting with Crystal/Mount.

Statistical Analysis. Comparison of multiple means was performed with InStat's one-way analysis of variance (ANOVA) (GraphPad Inc., San Diego, Calif.). All F statistics and P values for one-way ANOVAs are provided in the text. Comparison of individual drug treatments to the control treatments was performed with unpaired t-test. All p values for unpaired t-tests are provided in the text.

Results

Figure 2:
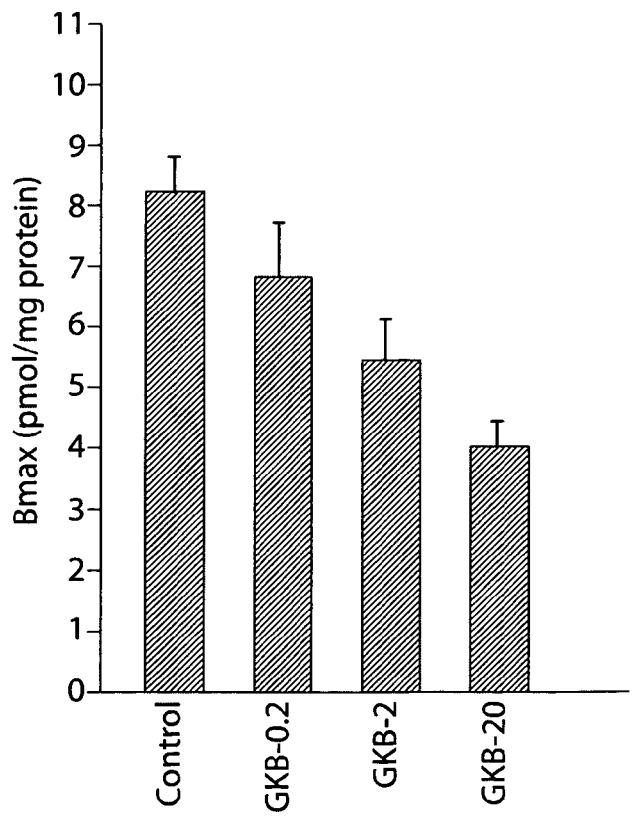
FIG. 2. Effect of various concentrations of GKB on MDA-231 PBR ligand binding capacity. MDA-231 cells were cultured as described under Materials and Methods. Cells were treated with the indicated concentrations of GKB for 48 hours. At the indicated time periods cells were then collected and PBR ligand binding characteristics were determined by Scatchard analysis. Data points represent the mean±S.D. of two independent experiments carried out in triplicate.

EGB 761® and GKB reduce the PBR Ligand Binding Capacity of the MDA-231 Human Breast Cancer Cells. FIG. 1 shows that increasing concentrations of the injectable form of EGB 761® inhibit in time-dependent manner the PBR ligand binding capacity (Bmax), determined using saturation isotherms with the radiolabeled ligand PK 11195 followed by Scatchard analysis of the data. Similar results were obtained using isolated GKB (FIG. 2). Interestingly, EGB 761® and GKB decreased PBR levels by 66% of control values. No significant effects on the receptor affinity (Kd) could be seen (5.8±1.4 pmol/mg protein, n=12).

Figure 3:
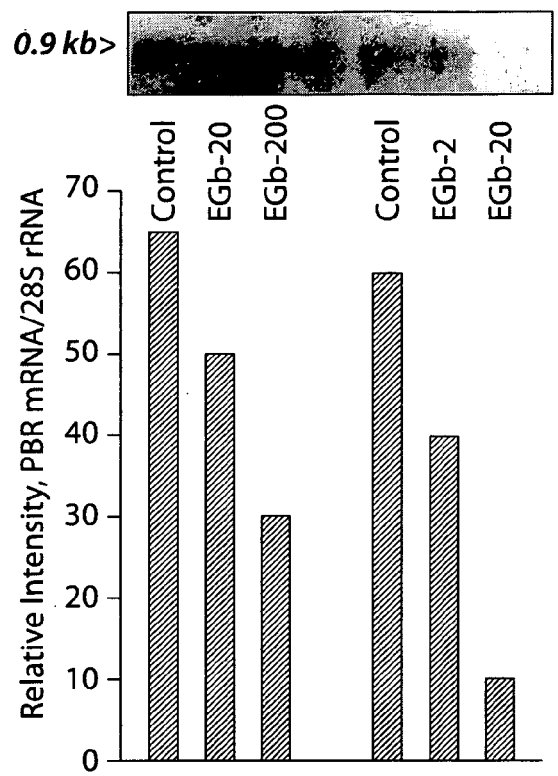
FIG. 3. Effect of EGB 761® and GKB on PBR mRNA levels in MDA-231 cells. Cells were treated for 48 hours without or with either 20 (EGb-20) or 200 (EGb-200) μg/ml EGB 761® or 2 (GKB-2) or 20 (GKB-20) μg/ml GKB. At the end of the incubation total RNA was isolated and loaded onto a 1% formaldehyde gel at a concentration of 10 μg/lane. Northern blots were incubated with $^{32}$P-labeled hPBR probe and exposed to XOMAT Kodak film. Top, autoradiogram of the blot. PBR migrates at 0.9 Kb. Bottom, relative intensity of the PBR mRNA/28S ribosomal RNA visualized by ethidium bromide staining. The autoradiogram and PBR mRNA quantitation represent one out of two independent experiments.

EGB 761® and GKB reduce the PBR mRNA Expression in MDA-231 Human Breast Cancer Cells. RNA (Northern) blot analysis was performed in order to determine if the differences seen in PBR ligand binding between the control and the EGB 761®- or GKB-treated cells reflect an effect on PBR mRNA expression. As shown in FIG. 3, both EGB 761® and GKB reduced PBR mRNA levels. This result fits with the results presented above on the PBR ligand binding expression.

Figure 4:
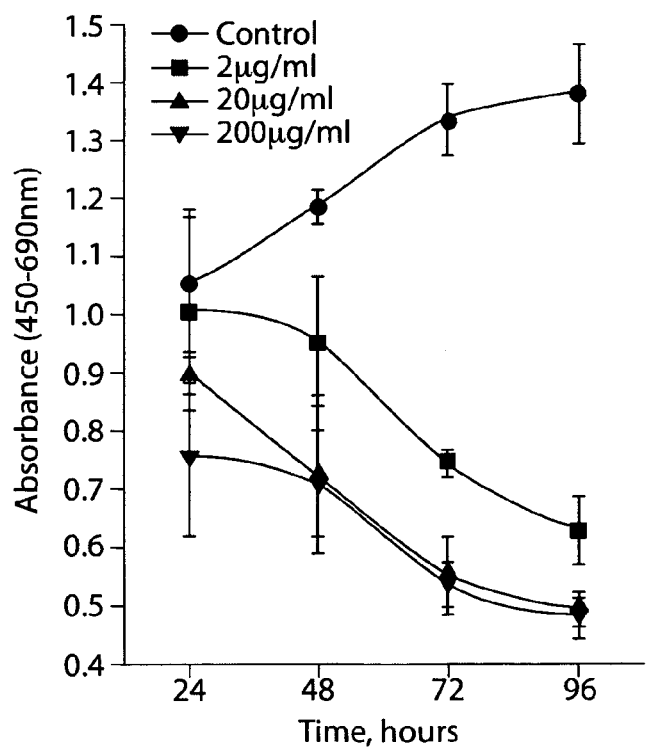
FIG. 4. Effect of EGB 761 ® on MDA-231 cell proliferation. MDA-231 cells grown in 96-well plates were washed with PBS and cultured in media supplemented with 10% FBS in the presence or absence of the indicated concentrations of EGB 761®. 4 h prior to the end of incubation, bromodeoxyuridine (BrdU) was added to each well. Incorporation of BrdU was measured at 450 nm (reference=700 nm). Data points represent the mean±S.D. of four independent experiments carried out in quadruplicate. One-way ANOVA indicates that MDA-231 cell proliferation was significantly altered by treatment with EGB 761® at 48, 72 and 96 h timepoints (P<0.0001).
Figure 5:
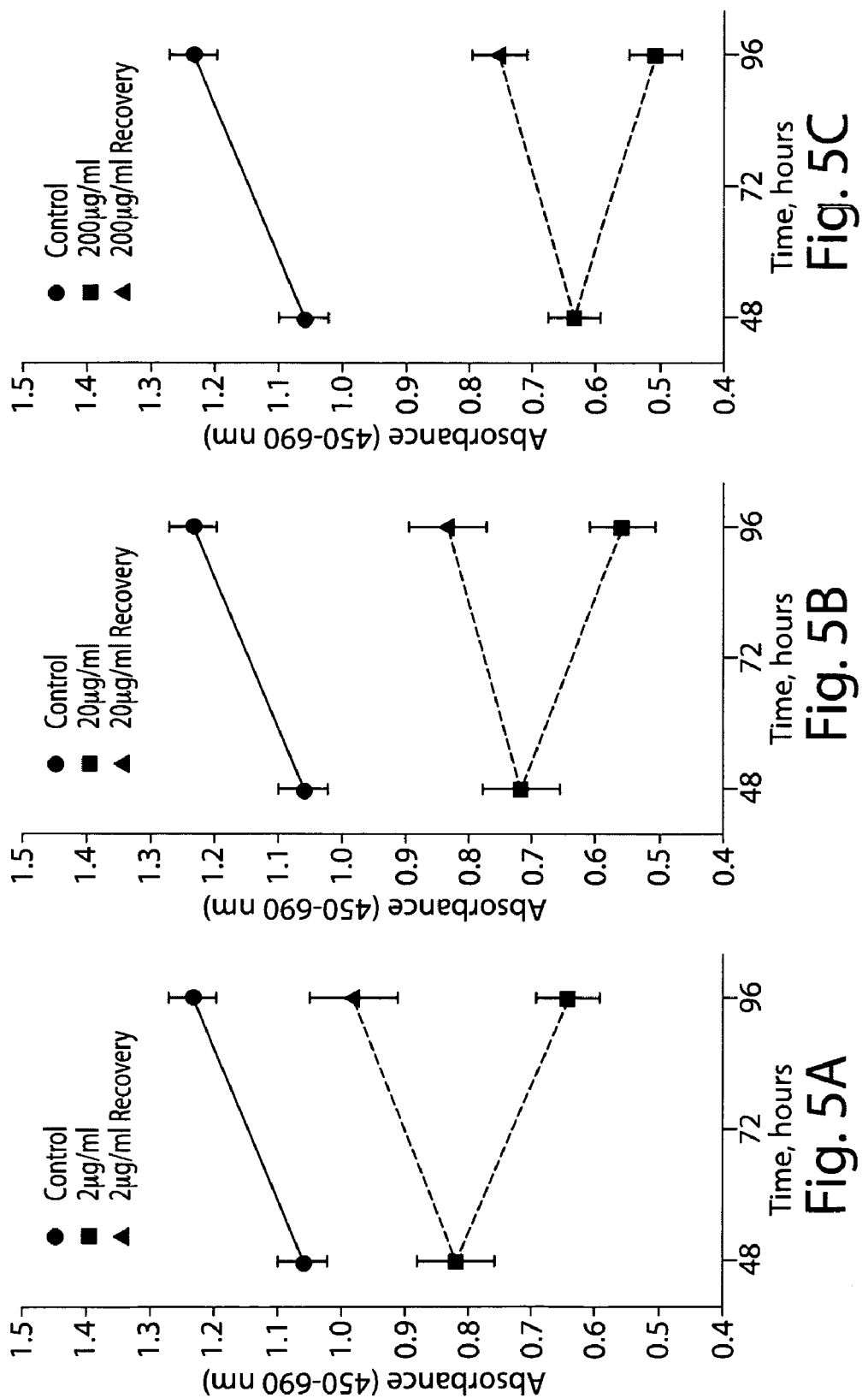
FIG. 5 Right, Middle, Left. Recovery of MDA-231 cell proliferation upon removal of EGB 761®. MDA-231 cells grown in 96-well plates were washed with PBS and cultured in media supplemented with 10% FBS in the presence or absence of 2 (Left), 20 (Middle) or 200 (Right) μg/ml EGB 761® for 48 h. At the end of the treatment the cells were washed and incubated in EGB 761®-free media for 48 h. 4 h prior to the end of incubation, bromodeoxyuridine (BrdU) was added to each well. Incorporation of BrdU was measured at 450 nm (reference=700 nm). Data points represent the mean±S.D. of two independent experiments carried out in quadruplicate.
Figure 6:
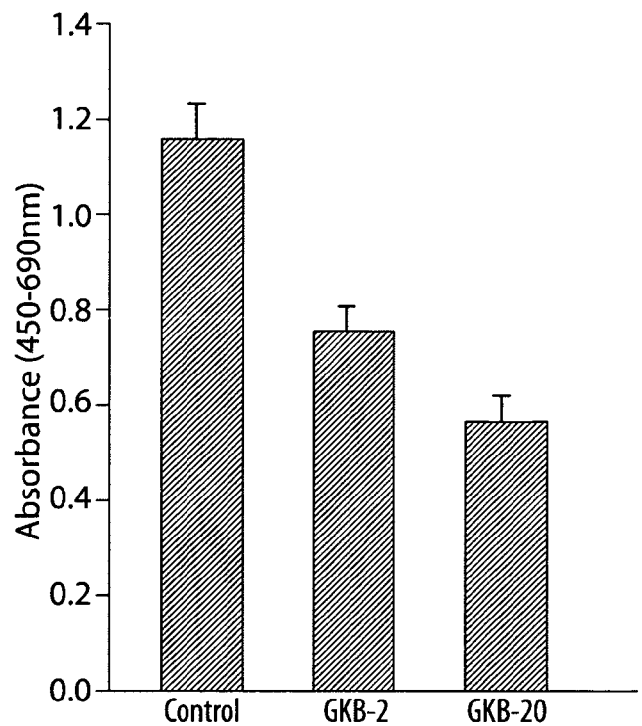
FIG. 6. Effect of GKB on MDA-231 cell proliferation. MDA-231 cells grown in 96-well plates were washed with PBS and cultured in media supplemented with 10% FBS in the presence or absence of either 2 μg/ml or 20 μg/ml GKB for 48 hours. 4 h prior to the end of incubation, bromodeoxyuridine (BrdU) was added to each well. Incorporation of BrdU was measured at 450 nm (reference=700 nm). Data points represent the mean±S.D. of two independent experiments carried out in quadruplicate. One-way ANOVA indicates that MDA-231 cell proliferation was significantly altered by treatment with GKB (P<0.0001).

EGB 761® and GKB Inhibit MDA-231 Cell Proliferation. Using the Bromodeoxyuridine (BrdU) Cell Proliferation ELISA (Boehringer-Mannheim, Indianapolis, Ind.), we examined the effect of increasing concentrations of EGB 761® on MDA-231 cell proliferation. FIG. 4 shows that EGb-761 inhibits in a concentration- and time-dependent manner the MDA-231 cell proliferation. This effect of EGB 761® was reversible, even for the highest concentration of EGB 761® used. (FIG. 5). Incubation of MDA-231 cells for 48 hours with EGB 761®, followed by washing and incubation for another 48 hours in EGB 761®-free medium, resulted in the recovery of the MDA-231 proliferative activity. Increasing concentrations of GKB also inhibited the MDA-231 cell proliferation after 48 hours treatment (FIG. 6).

Figure 7:
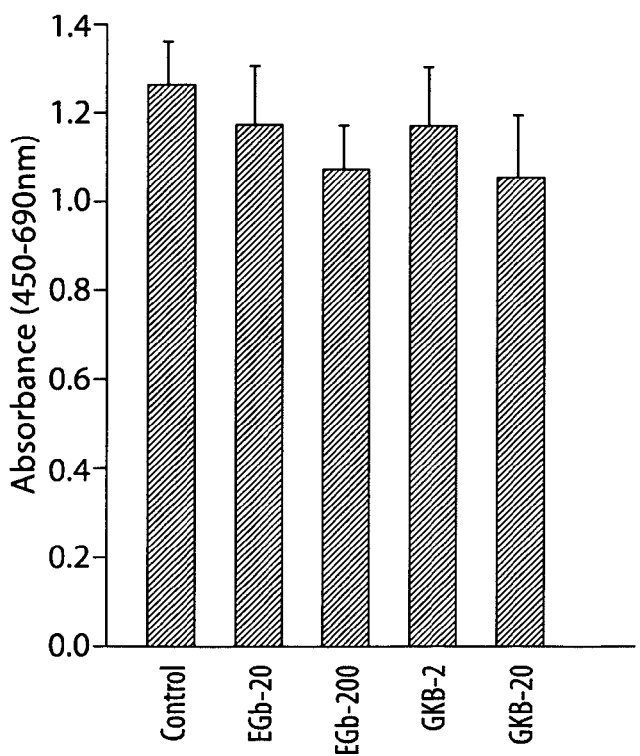
FIG. 7. Effect of EGB 761® and GKB on MCF-7 cell proliferation. MCF-7 cells were grown in 96-well plates as described in FIG. 4 for the MDA-231 cells. MCF-7 cells were treated for 48 hours without or with either 20 (EGb-20) or 200 (EGb-200) μg/ml EGB 761®, or 2 (GKB-2) or 20 (GKB-20) μg/ml GKB. 4 h prior to the end of incubation, bromodeoxyuridine (BrdU) was added to each well. Incorporation of BrdU was measured at 450 nm (reference=700 nm). Data points represent the mean±S.D. of two independent experiments carried out in quadruplicate. One-way ANOVA indicates that MCF-7 cell proliferation was altered to a lesser degree than the MDA-231 cell proliferation by treatment with EGB 761® or GKB.

EGB 761® and GKB Do Not Have The Same Level of Inhibition Against MCF-7 Cell Proliferation as They Do Against MDA-231 Cell Proliferation. Compared to the MDA-231 cells, the non-aggressive MCF-7 cells contain extremely low (<60 fold) PBR levels, as determined by both ligand binding studies and mRNA analyses, we examined whether EGB 761® and GKB affect the MCF-7 cell proliferation rate to the same degree as it affects MDA-231 cell proliferation rate. FIG. 7 clearly shows that neither EGB 761® nor GKB affect MCF-7 cell proliferation to the same degree as they affect the MDA-231 cell proliferation.

Figure 8:
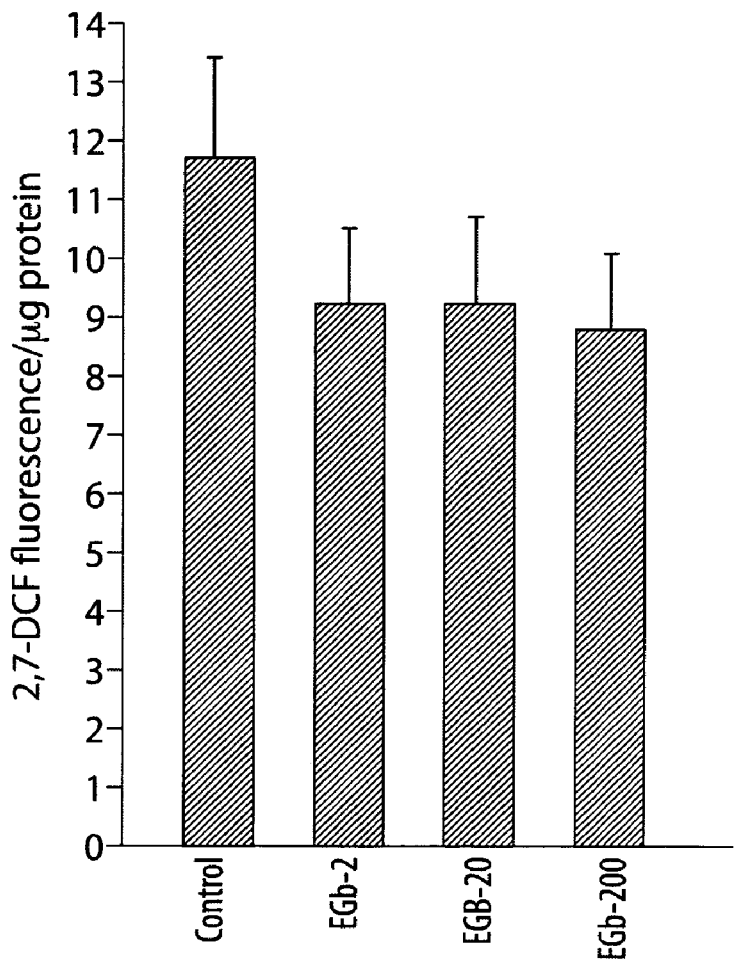
FIG. 8. Effect of EGB 761® on MDA-231 cell free radical production. MDA-231 cells were treated for 48 hours with 2 (EGb-2), 20 (EGb-20) or 200 (EGb-200) μg/ml of EGB 761®. The cells were then washed and the levels of cellular oxidative stress were measured using the fluorescent probe DCF as described under Materials and Methods. Results shown are means±S.D. (n=4). Statistical analysis indicated that the effect of EGB 761® was not significant.

EGB 761® Does Not Affect MDA-231 Free Radical Levels. Recent in vivo and in vitro studies demonstrated that the terpene constituents of EGB 761®, including GKB, have anti-oxidant properties. In order to determine whether the anti-proliferative effect of EGB 761® was due to its anti-oxidant properties, we determined the free radical levels in MDA-231 cells treated with and without increasing concentrations of EGB 761® (FIG. 8). Although a 20% decrease in free radical levels could be seen, this effect was neither statistically significant nor dose-dependent, indicating that the effect seen was not due to an EGB 761®-induced decrease of free radical levels in the cells.

Figure 9:
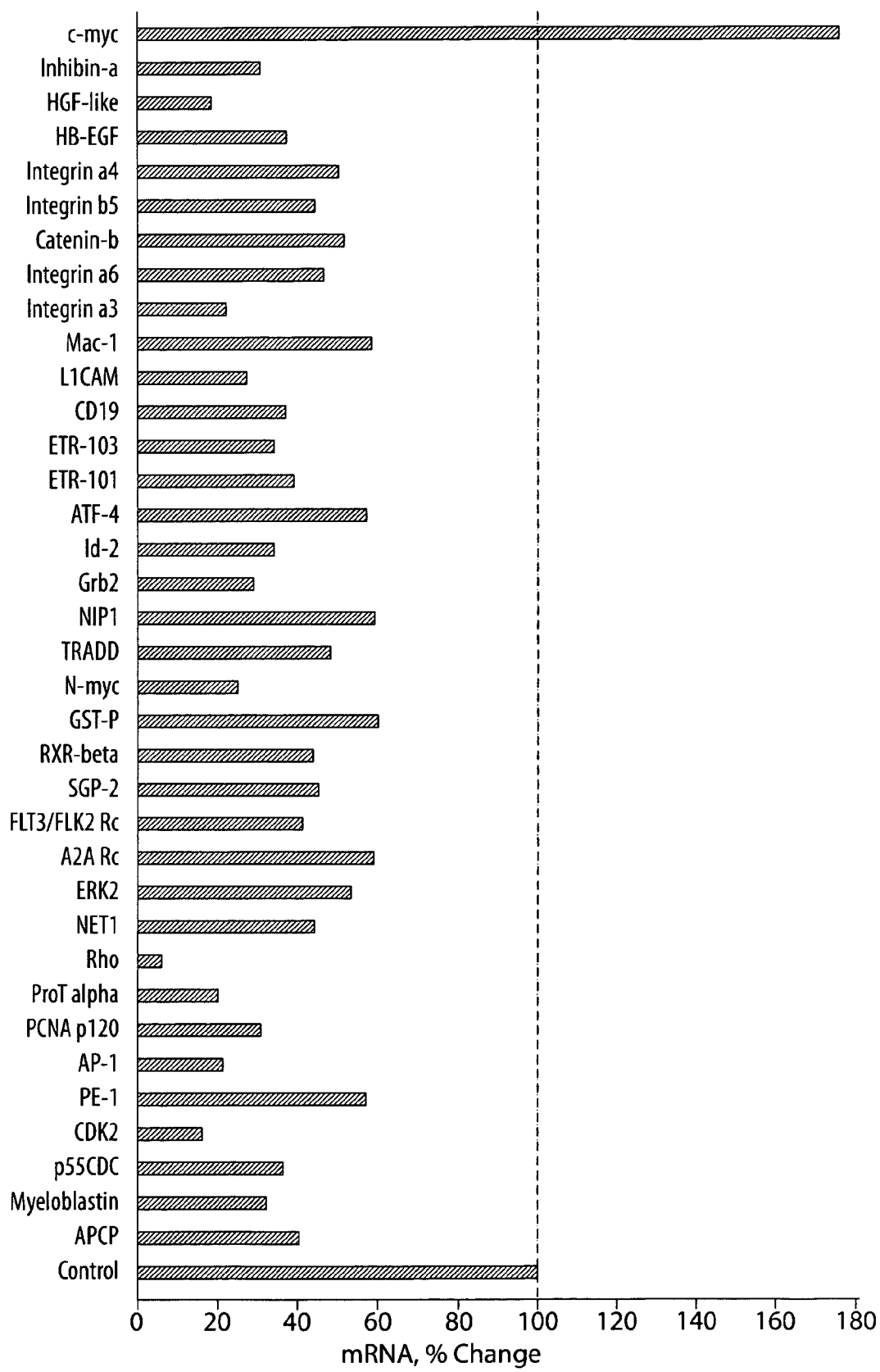
FIG. 9. Transcriptional response to EGB 761® suggests an effect on genes involved in cell proliferation. Results shown represent quantitative analysis of the Atlas human cDNA expression array containing 588 PCR-amplified cDNA fragments (Clontech Inc.). mRNAs were obtained from control or EGB 761® (20 μg/ml) treated, for 48 h, MDA-231 cells. For normalizing the mRNA abundance, the densitometric values obtained from image analysis were normalized using the housekeeping genes provided in the array. Only consistent significant changes above 30% were considered.

EGB 761® Regulates the MDA-231 Transcriptional Program Related to Cell Proliferation. The results presented above indicate that EGB 761® and GKB inhibit PBR expression and cell proliferation in the PBR-rich and highly aggressive MDA-231 breast cancer cells. The non-aggressive MCF-7 cells, which contain extremely low PBR levels, did not respond to EGB 761® treatment to the same degree as that of the MDA-231 breast cancer cells. In order to determine whether the effect of EGB 761® (20 µg/ml for 48 hours) on MDA-231 cells was specific for PBR or whether other genes involved in cell proliferation were affected by the treatment, we used a cDNA array representing 588 distinct human genes. As noted under Materials and Methods, experimental variations were corrected using the ratios of gene expression versus the internal controls. The effect of the EGB 761® treatment on each gene product is expressed as % of control (untreated) cells. Only consistent changes above 30% of control values are presented in FIG. 9 and Table I.

Figure 10:
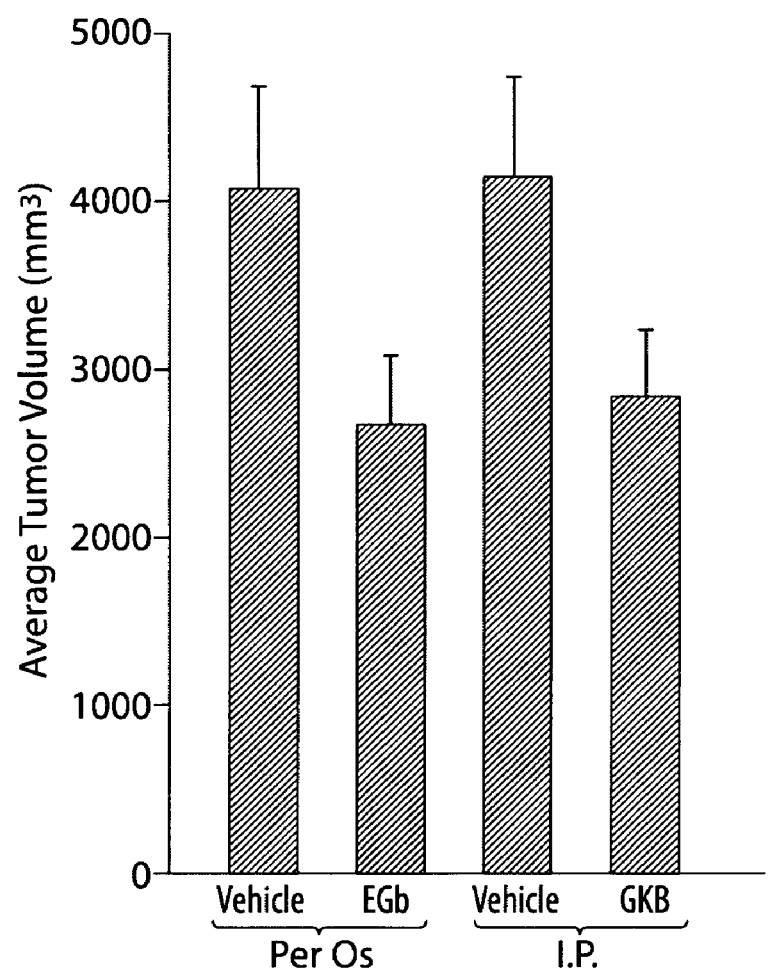
FIG. 10. Growth of MDA-231 xenografts in nude mice following either EGB 761® or GKB treatments. Animals were treated either orally with 50 mg/kg EGB 761® or ip with 1 mg/kg GKB once a day for a month starting with 100–150 mm$^3$ volume MDA-231 tumors. After the end of the treatment the animals were kept for 30 more days and then the animals were sacrificed on day 60. Data shown are means±S.E.M. (n=10). Statistical analysis indicated that the effects of EGB 761® and GKB were significant compared to their respective controls (p<0.05).
Figure 11:
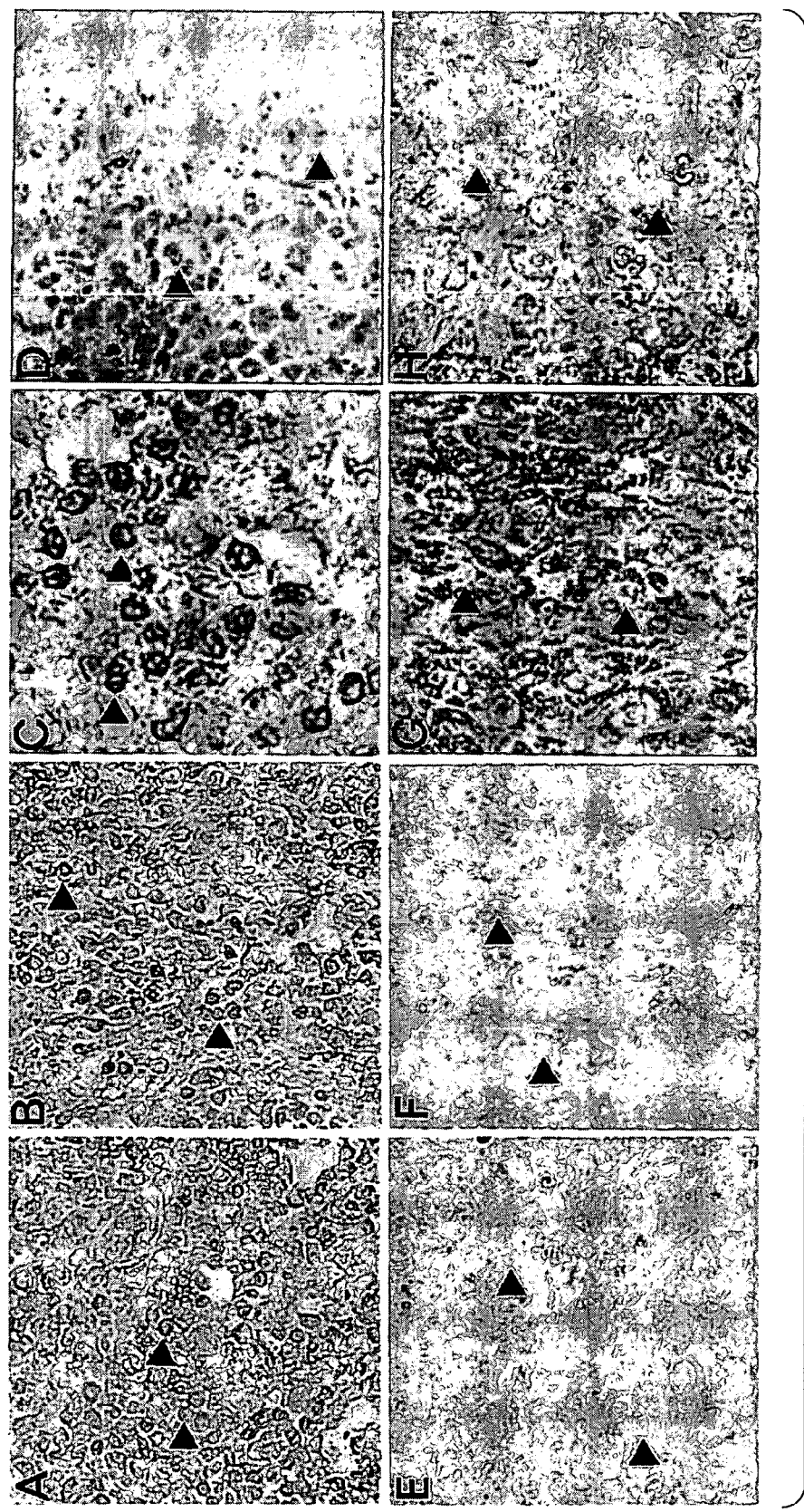
FIG. 11 A, B, C, D, E, F, G, H. PBR expression in MDA-231 xenografts from control and EGB 761® or GKB treated animals. Formalin embedded sections of MDA-231 xenografts were immunostained with an anti-PBR antiserum at 1:500 dilution as described in the Materials and Methods section. MDA-231 tumors were obtained from animals treated with vehicle (A–D), 50 mg/kg EGB 761® per os (E, G), or 1 mg/kg GKB ip (F, H). A shows cells found in the middle of a tumor obtained from vehicle-treated animals where the nuclear localization of the PBR protein can be easily seen (see arrowheads). B shows the immunostaining seen in cells present in the edge of the tumor obtained from vehicle-treated animals. A higher magnification of the immunostaining seen in the cells present in the edge of the tumor obtained from vehicle-treated animals is shown in C. D represents a control treated with a non-specific antiserum. E shows the PBR immunostaining in cells found in the middle of the tumor obtained from animals treated with EGB 761®. F shows the PBR immunostaining in cells found in the middle of the tumor obtained from animals treated with GKB. G shows the PBR immunostaining in cells found in the edge of the tumor obtained from animals treated with EGB 761®. H shows the PBR immunostaining in cells found in the middle of the tumor obtained from animals treated with GKB. Arrowheads indicate nuclei. Magnification is ×75 for A, B, C, E, F, G, and H and ×150 for C.

Biological Evaluation of the Effect of EGB 761® and GKB in Vivo In order to assess the effect of EGB 761® and GKB on tumor cell proliferation and PBR expression in an in vivo setting we used the mammary fat pad xenograft implantation model (See Medina, D., J. Mamm. Gland. Biol. Neopl. 1:5–19, 1996). FIG. 10 shows that 30 days treatment with either 50 mg/kg EGB 761® or with 1 mg/kg GKB resulted in a 35% (p=0.037) and 32% (p=0.043) decrease in tumor size, measured a month after the end of the treatment, respectively. These treatments did not affect the animal body weight (data not shown). Considering these in vitro data on the effect of EGB 761® and GKB on PBR expression in MDA-231 cells, we examined whether EGB 761® and GKB also decreased PBR expression in the MDA-231 xenografts. FIG. 11(A–D) shows horseradish peroxidase (HRP) staining of the PBR antiserum used to detect the 18,000 molecular weight protein in MDA-231 xenografts from vehicle-treated animals. The hematoxylin counterstain was omitted in order to distinguish the nuclear localization of PBR (19) in the tumors. FIG. 11A shows the middle of a tumor where the nuclear localization of the 18,000 PBR protein can be easily seen (see arrowheads). FIG. 11B shows the immunostaining seen in the edge of the tumor obtained from vehicle-treated animals. A higher magnification of the immunostaining seen in the edge of the tumor obtained from vehicle-treated animals is shown in FIG. 1C, and a control treated with a non-specific antiserum is shown in FIG. 11D. Treatment with either EGB 761® (FIG. 11E) or GKB (FIG. 11F) reduced the nuclear PBR expression present in cells found in the middle of the tumor. Interestingly, treatment with either EGB 761® (FIG. 11G) or GKB (FIG. 11H) also eliminated the nuclear PBR expression present in the cells at the edge of the tumors. However, in the later case cytosolic immunostaining could be seen (FIGS. 11G and H). These data were replicated in sections taken from xenografts grown in three separate animals.

It is of interest to note that even in the presence of high concentrations of either EGB 761® or GKB, PBR levels and rates of cell proliferation could not be reduced below 30% of normal values. This suggests that there is a minimum of PBR required to maintain membrane integrity and cell function. It should be also noted that even at the highest concentrations used, neither EGB 761® nor GKB were toxic for the cells, because cell proliferation recovered upon removal of the compounds. These data suggest that these compounds are cytostatic and not cytotoxic. Additional cytotoxicity assays indicated that under the same conditions neither EGB 761® nor GKB induced any significant cell death.

The absence of any significant decrease in the amount of reactive oxygen species produced in the MDA-231 cells by EGB 761® or GKB suggests that their anti-oxidant properties were not responsible for decreasing PBR expression and cell proliferation in the MDA-231 cells. These results indicate that these compounds may regulate PBR gene transcription either directly or indirectly.

The finding that EGB 761® and GKB decreased PBR expression and cell proliferation in the highly aggressive, nuclear PBR-expressing MDA-231 cells, but did not affect the non-aggressive MCF-7 cells, which have extremely low PBR levels and are devoid of nuclear PBR, to the same degree as they did for MDA-231 cells, provides an additional support to the hypothesis that the presence of PBR may be a determinant factor for the aggressive phenotype of breast tumor cells. Moreover, this observation further demonstrates the specificity of the effect of EGB 761® and GKB on targeting the regulation of PBR expression. This later finding brought us to two key questions raised by the current study: is the expression of other genes regulated by EGB 761®? is there a transcriptional program activated or inhibited by EGB 761®, where PBR is at the origin or a part of a cascade of events, responsible for altering the proliferation rate of MDA-231 cells? To address these questions, we utilized the Atlas Human cDNA Expression Array. As indicated in Table I, treatment of MDA-231 cells with the EGB 761® extract induced alterations in the transcriptional expression of 36 out of 588 genes examined. Not surprisingly, the vast majority of the affected genes have close ties to either cell proliferation, differentiation, or apoptosis. Perhaps the most telling of the effects EGB 761® has on the MDA-231 cell line is the down-regulation of the p120 proliferation-cell nuclear antigen. p120 is used as a prognostic indicator in breast cancer patients and prostate adenocarcinomas (Perlaky, L., et al., Cancer Res., 52: 428–436, 1992; Zhuang, S. H. et al., Endocrinology, 139: 1197–1207, 1998). More importantly, however, p120 is an immunocytochemical marker of proliferating cells. Down-regulation of this proliferation marker by 68% thus confirms our data demonstrating that EGB 761® inhibits MDA-231 cell proliferation.

Using a human cDNA expression array we examined the effect of the EGB 761 treatment on the expression of 588 genes in MDA-231 cells. We found that the treatment increased the expression of the c-Myc protooncogene and decreased the expression of 35 gene products, including oncogenes (AP-1, PE-1, RhoA, n-Myc), cell cycle regulators (CDK2, p55CDC, PCNA p120), signal transduction modulators (NET1, ERK2), apoptosis-related products (SGP-2, NIP1) receptors (A2A, RXR-beta, Grb2), transcription factors (Id-2, ATF4, ETR101, ETR-103), growth factors (HB-EGF, HGF-like), and cell adhesion molecules (CD19, L1CAM, integrins α3, α4, α6, β5, Mac-1, β-catenin) which are directly involved in various pathways regulating cell proliferation. Considering that the compounds tested were effective only on the MDA-231-cells, which express high levels of PBR, these data suggest that the expression of nuclear PBR may be a determining factor for a tumor cell to acquire an aggressive and invasive phenotype.

TABLE I

Effect of EGB 761 ® on MDA-231 gene expression examined using the Atlas human cDNA expression array as described under Materials and Methods.

| Name | % Change | Function | References |
|---|---|---|---|
| *Oncogenes and Tumor Suppressers* | | | |
| c-Myc | +75% | basic helix-loop-helix-leucine zipper transcription factor Myc/Max heterodimers induce cell-cycle progression, apoptosis, and malignant transformation | (37) |
| c-Jun | −78% | part of the AP-1 transcription factor that regulates genes involved in cell proliferation | (38) |
| RhoA | −93% | GTP-binding protein that is an important regulator of cell proliferation | (39) |
| | | RhoA inactivation inhibits HL60 cell proliferation | (40) |
| APC | −59% | APC mutations are associated with both hereditary and sporadic colorectal cancers | (41) |
| | | a negative post-translational regulator of β-catenin | (42) |
| PE-1 | −42% | transcription factor | (43) |
| *Cell Cycle Control Proteins* | | | |
| Prothymosin-α | −79% | acidic nuclear protein that is upregulated in proliferating thymocytes, lymphocytes from leukemia patients, and in malignant breast lesions | (44) |
| Myeloblastin | −66% | a serine protease involved in leukemia cell differentiation | (45) |
| p55CDC | −63% | similar to mitosis regulators CDC4 and CDC20 expression positively correlated with cell proliferation status | (46) |
| p120 Proliferating-cell Nuclear Antigen | −68% | nucleolar protein expressed in proliferating cells | (47) |
| | | a prognostic indicator for breast cancer patients and prostate adenocarcinoma | (48) |
| CDK2 | −83% | cyclin-dependent tyrosine kinase involved in progression through the cell cycle | (49) |
| | | cyclin E/Cdk2 inactivates the retinoblastoma tumor suppresser to allow the cell to progress to S phase | (50) |
| | | Vitamin D inhibition of LNCaP cell proliferation coincided with a reduction in Cdk2 activity | |
| *Intracellular Transducers* | | | |
| NET1 | −55% | RhoA-specific guanine exchange factor NIH3T3-transforming protein | (51) |
| ERK2 | −46% | member of the extracellular signal-related protein kinase family activated upon cell stimulation | (52) |
| *Apoptosis-Related Proteins* | | | |
| Adenosine A2A Receptor | −40% | G protein-coupled receptor involved in the cAMP signaling pathway | (53) |
| Flt3 ligand | −58% | ligand for the Flt3 cytokine receptor tyrosine kinase induces proliferation of leukemic myeloid cells | (54) |
| Grb2 | −70% | an adapter protein that links receptor tyrosine kinases to the Ras/MAPK signaling pathway via its SH2 domain | (55) |
| Clusterin | −54% | a glycoprotein associated with cell adhesion and apoptosis | (56, 57) |
| | | increased expression is linked to Alzheimer's disease | (58) |
| RXR-β | −55% | retiniod-activated transcription factor | (59) |
| | | inhibition of chondrocyte proliferation by retinoic acid causes a reduction in RXR-β mRNA expression | (60) |
| Glutathione S-transferase P | −39% | a multi-drug resistance gene that is overexpressed in various human tumors | (61, 62) |
| | | chemical inhibition of GST-P inhibits proliferation of Jurkat T cells | (63) |
| N-Myc | −74% | c-myc family member associated with early-onset retinoblastoma | (64) |
| TRADD | −51% | TNFR-associated death domain protein involved in TNFR-induced cell growth and differentiation | (65) |

TABLE I-continued

Effect of EGB 761 ® on MDA-231 gene expression examined using the Atlas human cDNA expression array as described under Materials and Methods.

| Name | % Change | Function | References |
|---|---|---|---|
| NIP-1 | −40% | originally described as a yeast nuclear transport protein | (66) |
| | | part of the translation initiation factor 3 (eIF3) core complex | (67) |
| | | DNA-Binding/Transcription Factors | |
| Id-2 | −65% | a member of the Id helix-loop-helix family of transcriptional inhibitors | (68) |
| | | involved in proliferation of human pancreatic cancer cells | |
| ATF4 | −42% | a member of the ATF/CREB family of transcription factors | (69) |
| | | regulates Ras-induced transformation of NIH3T3 cells | |
| ETR103 | −65% | a macrophage-associated immediate early gene | (70) |
| ETR101 | −60% | a lymphocyte-associated immediate early gene | (71) |
| | | Cell Surface Antigens and Adhesion Molecules | |
| CD19 B-lymphocyte Antigen | −62% | B-lymphocyte integral membrane protein | (72) |
| | | expression is down-regulated during retinoid-inhibition of lymphoblastoid B-cell proliferation | |
| L1CAM | −72% | neural cell adhesion molecule | (73) |
| | | increased L1CAM expression is associated with high-grade migration of glioma cells | |
| β-catenin | −58% | involved in cadherin-mediated cell-cell interactions | (74) |
| | | interacts with the TCF/LEF transcription factors in the Wnt signaling pathway | |
| Integrin Subunits | | | |
| αM | −41% | mediates cellular adherence of human neutrophils with LFA-1β | (75) |
| | | α subunit of the elastase receptor | |
| β5 | −55% | β subunit of the vitronectin receptor (VR) | (76) |
| | | involved in cessation of oligodendrocyte proliferation | (77) |
| | | involved in murine retinal angiogenesis | (78) |
| α4 | −49% | cross-linking α4 integrins inhibits LB lymphoma cell proliferation | (79) |
| | | also involved in metastasis of melanoma and lymphoma cells | (80) |
| α3 | −77% | a functionally perturbing α3 integrin antibody inhibits human epithelial cell proliferation | (81) |
| α6 | −53% | overexpression of α6 integrin collaborates with ErbB2 to induce a more malignant phenotype in NIH3T3 cells | (82) |
| | | Extracellular Signaling/Communication Proteins | |
| Macrophage Colony-stimulating Factor-1 (CSF-1) | −31% | regulates the proliferation, differentiation, and survival of monocytes, macrophages and their precursors | (83) |
| | | initiates a mitogenic signal that is required throughout G1 phase | (84) |
| | | CSF-1 stably transfected ovarian granulosa cells exhibit enhanced cell proliferation | |
| Heparin-binding EGF-like Growth Factor (HB-EGF) | −62% | overexpressed in numerous human glioma cell lines and in a majority of glioblastomas | (85) |
| | | stimulates human glioma cell proliferation | |
| Hepatocyte Growth Factor-like Protein (HGFLP) | −81% | a transmembrane protein tyrosine kinase found to be overexpressed in hepatoblastoma and in human primary liver carcinoma | (86) |
| | | induces proliferation and migration of murine keratinocytes | (87) |
| Inhibin α | −69% | a member of the inhibin family of heterodimeric growth factors | (88) |
| | | inhibin α is a marker of trophoblastic neoplasia and is highly expressed in virilizing adenomas | (89) |

Two members of the Myc family of transcription factors, c-Myc and n-Myc, were found to be grossly altered in this experiment. Expression of the proto-oncogene c-Myc was increased by 75% while expression of n-Myc was reduced by 74%. Both of these genes are overexpressed in several cancer types (Kim, C. J., et al., Virchows Arch., 434: 301–305, 1999; Dang, C. V., Mol. Cel. Biol., 19: 1–11, 1999) and are strongly correlated with tumor cell proliferation. Previous studies have shown that arrest of neuroblastoma cell growth by the tyrosine kinase inhibitor genistein is accompanied by down-regulation of n-Myc expression. This data fits extremely well with our cell proliferation and n-Myc data. Overexpression of c-Myc, however, is associated with a stimulation of cell proliferation in normal serum conditions. Overexpression of c-Myc induces cell death in the absence of serum or other survival factors. Taken together the data implies that deregulation of c-Myc expression requires the altered expression of other genes, as well.

In our microarray experiment, we discovered the deregulated expression of several other c-Myc-related genes. One such gene, prothymosin α (proT α), is induced by c-Myc. However, expression of proT α is reduced by 79% rather than increased, as might be predicted by up-regulation of c-Myc. Further, expression of other c-Myc target genes such as cdc25A, cyclin A, and cyclin E are unaffected by treatment of MDA-231 cells with EGB 761®, suggesting either a treatment-specific or a cell line-specific short circuit in c-Myc-regulated gene transcription. Other data gathered from the microarray experiment further supports this hypothesis. c-Myc transcriptional regulation is under the control of APC and β-catenin. However, both of these genes are down-regulated by EGB 761® in MDA-231 cells (59 and 58%, respectively) while c-Myc is up-regulated. While some of this data appears to be contradictory, much of the published data on the role of c-Myc in cell proliferation, differentiation, and cell death also appears contradictory.

Similar to the altered regulation of c-Myc and Myc-related proteins by EGB 761®, the microarray experiment exposed disruption of several signaling molecules. EGB 761® treatment resulted in a 93% reduction in the expression of RhoA, a gene encoding a GTP-binding protein involved in numerous cellular phenomena, and a 55% reduction in NET1 expression, a RhoA-specific guanine exchange factor. Interestingly, RhoA has been demonstrated to regulate cyclin E/Cdk2 activity in fibroblasts. Activation of cyclin E/Cdk2 complex is crucial to the progression of the cell cycle from G1 to S-phase. Regulation of cyclin E/Cdk2 activity has also been demonstrated by c-Myc. Although the significance of these two phenomena is not immediately obvious, it should be noted that expression of Cdk2 is reduced by 83% by EGB 761®.

Other important signaling molecules are also down-regulated by EGB 761®. Expression of the adapter molecule Grb2 is reduced by 70%. Grb2 plays an important role in cellular signaling by physically linking signal transducers such as receptor tyrosine kinases to the Ras/MAPK pathway. With regard to the MAPK pathway, expression of the MAP/ERK family member ERK2 is down-regulated by 46% and expression of the c-Jun transcription factor is reduced by 78%. Interestingly, it has been reported that EGB 761® is a suppressor of AP-1 transcription factor stimulated by phorbol esters. These data imply that the effects of EGB 761® on MDA-231 cell proliferation are accompanied by a broad reduction in mRNAs with functional relationships with one another.

Another interesting finding from the microarray experiment is the reduced expression of several integrins. The integrins are a large family of cell-cell and cell-extracellular matrix adhesion receptors that are composed of two transmembrane glycoprotein subunits, one α-and one β-subunit. All of the integrins represented in Table I are involved in the regulation of cell proliferation in some way. For example, integrin αM is part of the elastase receptor. ONO-5046, an elastase inhibitor, suppresses the proliferation of polyoma virus- and Kirsten sarcoma virus-transformed BALB/c3T3 cells and of Capan-1 pancreatic carcinoma cells. Moreover, integrin α4 has been implicated in the accumulation of distal metastases in melanoma, sarcoma, and lymphoma cell models. It is important to emphasize that integrins function as heterodimers of one α- and one β-subunit. Reduced expression of either the α- or the β-subunit is clearly important in the regulation of integrin receptor function.

The expression of some key growth factor genes, such as the hepatocyte growth factor-like and EGF-like growth factor, were also reduced by EGB 761®. It is possible that the EGB 761®-induced inhibition of cell proliferation may be due to the reduced expression of these growth factors that may act as autocrine regulators of cell growth.

EGB 761® and GKB are intended to be provided to recipient patient in an amount sufficient to combat cancer in said patient or in an amount sufficient to affect the expression (negatively or positively) of the gene products listed in Table 1, hereinabove. An amount is said to be sufficient to combat cancer if the dosage, route of administration, etc. of the EGB 761® and GKB are sufficient to influence such a response.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

EGB 761® and GKB can be formulated according to known methods to prepare pharmaceutically useful compositions, whereby these materials, or their functional derivatives are optionally combined in admixture with a pharmaceutically acceptable carrier vehicle. Suitable vehicles and their formulation, inclusive of other human proteins, e.g., human serum albumin, are described, for example, in Remington's Pharmaceutical Sciences ($16^{TH}$ ED., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles and nanocapsules or in macroemulsions. Such techniques are disclosed in Remington's Pharmaceutical Sciences (1980).

EGB 761® and isolated GKB can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of EGB 761® or isolated GKB in the compositions of this invention may be varied; however, it is necessary that the amount of the active ingredient be such that a suitable dosage form is obtained. The selected dosage depends upon the desired therapeutic effect, on the route of administration, and on the duration of the treatment. The dose can be administered as a single dose or divided into multiple doses. An effective dose amount of either EGB 761® or isolated GKB depends upon the condition being treated, the route of administration chosen and ultimately will be decided by the attending physician or veterinarian.

REFERENCES

37. Amati, B., Alevizopoulos, K., and Vlach, J. Myc and the Cell Cycle. Frontiers in Bioscience, 3: 250–268, 1998.
38. Huang, W. and Erikson, R. L. Signal Transduction. p. 161. Chapman and Hall, 1996.
39. Hu, W., Bellone, C. J., and Baldassare, J. J. RhoA stimulates p27(Kip) degradation through its regulation of cyclin E/CDK2 activity. J. Biol. Chem., 274: 3396–3401, 1999.
40. Aepfelbacher, M., Essler, M., Luber, D. Q., and Weber, P. C. ADP-ribosylation of the GTP-binding protein RhoA blocks cytoplasmic division in human myelomonocytic cells. Biochem. J., 308: 853–858, 1995.
41. Jeanteur, P. The role of APC in colon cancer: Zeroing in on Myc. Bulletin du Cancer (France), 85: 925–928, 1998.
42. Munemitsu, S., Albert, I., Souza, B., Rubinfeld, B., and Polakis, P. Regulation of intracellular beta-catenin levels by the adenomatous polyposis coli (APC) tumor-suppressor protein. Proc. Natl. Acad. Sci. U.S.A., 92: 3046–3050, 1995.
43. Klemsz, M., Hromas, R., Raskind, W., Bruno, E., and Hoffman, R. PE-1, a novel ETS oncogene family member, localizes to chromosome 1q21-q23. Genomics, 20: 291–294, 1994.
44. Gomez-Marquez, J., Segade, F., Dosil, M., Pichel, J. G., Bustelo, X. R., and Freire, M. The expression of prothymosin alpha gene in T lymphocytes and leukemic lymphoid cells is tied to lymphocyte proliferation. J. Biol. Chem., 264: 8451–8454, 1989.
45. Bones, D., Raynal, M. C., Solomon, D. H., Darzynkiewicz, Z., and Cayre, Y. E. Down-regulation of a serine protease, myeloblastin, causes growth arrest and differentiation of promyelocytic leukemia cells. Cell, 59: 959–968, 1989.
46. Kao, C. T., Lin, M., O'Shea-Greenfield, A., Weinstein, J., and Sakamoto, K. M. Over-expression of p55Cdc inhibits granulocyte differentiation and accelerates apoptosis in myeloid cells. Oncogene, 13: 1221–1229, 1996.
47. Landberg, G. and Roos, G. The Cell Cycle in Breast Cancer. APMIS, 105: 575–589, 1997.
48. Perlaky, L., Valdez, B. C., Busch, R. K., Larson, R. G., Jhiang, S. M., Zhang, W. W., Brattain, M., and Busch, H. Increased growth of NIH/3T3 cells by transfection with human p120 complementary DNA and inhibition by a p120 antisense construct. Cancer Res., 52: 428–436, 1992.
49. Zhuang, S. H. and Burnstein, K. L. Antiproliferative Effect of 1alpha,25-dihydroxyvitamin D3 in Human Prostate Cancer Cell Line LNCaP Involves Reduction of Cyclin-dependent Kinase 2 Activity and Persistent G1 Accumulation. Endocrinology, 139: 1197–1207, 1998.
50. Chan, A. M., Takai, S., Yamada, K., and Miki, T. Isolation of a novel oncogene, NET1, from neuroepithelioma cells by expression cDNA cloning. Oncogene, 12: 1259–1266, 1996.
51. Ahn, N. G. and Tolwinski, N. S. U0126: An Inhibitor of MKK/ERK Signal Transduction in Mammalian Cells. Promega Notes, 71: 4–13, 1999.
52. Coppee, F., Gerard, A. C., Denef, J. F., Ledent, C., Vassart, G., Dumont, J. E., and Parmentier, M. Early occurrence of metastatic differentiated thyroid carcinomas in transgenic mice expressing the A2a adenosine receptor gene and the human papillomavirus type 16 E7 oncogene. Oncogene, 13: 1471–1482, 1996.
53. Dehmel, U., Zaborski, M., Meierhoff, G., Rosnet, O., Birnbaum, D., Ludwig, W. D., Quentmeier, H., and Drexler, H. G. Effects of FLT3 ligand on human leukemia cells. I. Proliferative response of myeloid leukemia cells. Leukemia, 10: 261–270, 1996.
54. Benito, M., Valverde, A. M., and Lorenzo, M. IGF-1: a mitogen also involved in differentiation processes in mammalian cells. Int. J. Biochem. Cell Biol., 28: 499–510, 1996.
55. Chevalier, R. L. Effects of ureteral obstruction on renal growth. Semin. Nephrol., 15: 353–360, 1995.
56. Truong, L. D., Sheikh-Hamad, D., Chakraborty, S., and Suki, W. N. Cell Apoptosis and Proliferation in Obstructive Uropathy. Semin. Nephrol., 18: 641–651, 1998.
57. Choi-Miura, N. H. and Oda, T. Relationship between multifunctional protein "clusterin" and Alzheimer disease. Neurobiol. Aging, 17: 717–722, 1996.
58. Lotan, R. Retinoids and chemoprevention of aerodigestive tract cancers. Cancer Metastasis Rev., 16: 349–356, 1997.
59. Hagiwara, H., Inoue, A., Nakajo, S., Nakaya, K., Kojima, S., and Hirose, S. Inhibition of proliferation of chondrocytes by specific receptors in response to retinoids. Biochem. Biophys. Res. Commun., 222: 220–224, 1996.
60. Campos, L., Oriol, P., Sabido, O., and Guyotat, D. Simultaneous expression of P-glycoprotein and BCL-2 in acute myeloid leukemia blast cells. Leuk. Lymphoma., 27: 119–125, 1997.
61. Lacave, R., Coulet, F., Ricci, S., Touboul, E., Flahault, A., Rateau, J. G., Cesari, D., Lefranc, J. P., and Bemaudin, J. F. Comparative evaluation by semiquantitative reverse transcriptase polymerase chain reaction of MDR1, MRP and GSTp gene expression in breast carcinomas. Br. J. Cancer, 77: 694–702, 1998.
62. McCaughan, F. M., Brown, A. L., and Harrison, D. J. The effect of inhibition of glutathione S-transferase P on the growth of the Jurkat human T cell line. J. Pathol., 172: 357–362, 1994.
63. Kim, C. J., Chi, J. G., Choi, H. S., Shin, H. Y., Ahn, H. S., Yoo, Y. S., and Chang, K. Y. Proliferation not Apoptosis as a Prognostic Indicator in Retinoblastoma. Virchows Arch., 434: 301–305, 1999.
64. Newton, K., Harris, A. W., Bath, M. L., Smith, K. C., and Strasser, A. A dominant interfering mutant of FADD/MORT1 enhances deletion of autoreactive thymocytes and inhibits proliferation of mature T lymphocytes. EMBO J., 17: 706–718, 1998.
65. Gu, Z., Moerschell, R. P., Sherman, F., and Goldfarb, D. S. NIP1, a gene required for nuclear transport in yeast. Proc. Natl. Acad. Sci. U.S.A., 89: 10355–10359, 1992.
66. Phan, L., Zhang, X., Asano, K., Anderson, J., Vornlocher, H. P., Greenberg, J. R., Qin, J., and Hinnebusch, A. G. Identification of a translation initiation factor 3 (eIF3) core complex, conserved in yeast and mammals, that interacts with eIF5. Mol. Cell Biol., 18: 4935–4946, 1998.
67. Kleeff, J., Ishiwata, T., Friess, H., Buchler, M. W., Israel, M. A., and Korc, M. The helix-loop-helix protein Id2 is overexpressed in human pancreatic cancer. Cancer Res., 58: 3769–3772, 1998.
68. Mielnicki, L. M., Hughes, R. G., Chevray, P. M., and Pruitt, S. C. Mutated Atf4 suppresses c-Ha-ras oncogene transcript levels and cellular transformation in NIH3T3 fibroblasts. Biochem. Biophys. Res. Commun., 228: 586–595, 1996.
69. Shimizu, N., Ohta, M., Fujiwara, C., Sagara, J., Mochizuki, N., Oda, T., and Utiyama, H. A gene coding for a zinc finger protein is induced during 12-O-tetradecanoylphorbol-13-acetate-stimulated HL-60 cell differentiation. J. Biochem. (Tokyo.), 111: 272–277, 1992.
70. Shimizu, N., Ohta, M., Fujiwara, C., Sagara, J., Mochizuki, N., Oda, T., and Utiyama, H. Expression of a novel immediate early gene during 12-O-tetradecanoylphorbol-13-acetate-induced macrophagic differentiation of HL-60 cells. J. Biol. Chem., 266: 12157–12161, 1991.
71. Dolcetti, R., Zancai, P., Cariati, R., and Boiocchi, M. In vitro effects of retinoids on the proliferation and differentiation features of Epstein-Barr virus-immortalized B lymphocytes. Leuk. Lymphoma, 29: 269–281, 1998.
72. Tsuzuki, T., Izumoto, S., Ohnishi, T., Hiraga, S., Arita, N., and Hayakawa, T. Neural cell adhesion molecule L1 in gliomas: correlation with TGF-beta and p53. J. Clin. Pathol., 51: 13–17, 1998.
73. Young, C. S., Kitamura, M., Hardy, S., and Kitajewski, J. Wnt-1 induces growth, cytosolic beta-catenin, and Tcf/Lef transcriptional activation in Rat-1 fibroblasts. Mol. Cell Biol., 18: 2474–2485, 1998.
74. Cai, T. Q. and Wright, S. D. Human leukocyte elastase is an endogenous ligand for the integrin CR3 (CD11b/CD18, Mac-1, alpha M beta 2) and modulates polymorphonuclear leukocyte adhesion. J. Exp. Med, 184: 1213–1223, 1996.
75. De Deyne, P. G., O'Neill, A., Resneck, W. G., Dmytrenko, G. M., Pumplin, D. W., and Bloch, R. J. The Vitronectin Receptor Associates with Clathrin-coated Membrane Domains Via the Cytoplasmic Domain of its beta5 Subunit. J. Cell Sci., 111: 2729–2740, 1998.
76. Milner, R. and Ffrench-Constant, C. A developmental analysis of oligodendroglial integrins in primary cells: changes in alpha v-associated beta subunits during differentiation. Development, 120: 3497–3506, 1994.
77. Friedlander, M., Theesfeld, C. L., Sugita, M., Fruttiger, M., Thomas, M. A., Chang, S., and Cheresh, D. A. Involvement of integrins alpha v beta 3 and alpha v beta 5 in ocular neovascular diseases. Proc. Natl. Acad. Sci. U.S.A., 93: 9764–9769, 1996.
78. Bittner, M., Gosslar, U., Luz, A., and Holzmann, B. Sequence Motifs in the Integrin alpha4 Cytoplasmic Tail Required for Regulation of In Vivo Expansion of Murine Lymphoma Cells. J. Immunol., 161: 5978–5986, 1998.
79. Holzmann, B., Gosslar, U., and Bittner, M. alpha 4 integrins and tumor metastasis. Curr. Top. Microbiol. Immunol., 231:125–141, 1998.
80. Gonzales, M., Haan, K., Baker, S. E., Fitchmun, M., Todorov, I., Weitzman, S., and Jones, J. C. A Cell Signal Pathway Involving Laminin-5, alpha3beta1 Integrin, and Mitogen-activated Protein Kinase can Regulate Epithelial Cell Proliferation. Mol. Biol. Cell, 10: 259–270, 1999.
81. Falcioni, R., Antonini, A., Nistico, P., Di, S. S., Crescenzi, M., Natali, P. G., and Sacchi, A. Alpha 6 beta 4 and alpha 6 beta 1 integrins associate with ErbB-2 in human carcinoma cell lines. Exp. Cell Res., 236: 76–85, 1997.
82. Roussel, M. F. Regulation of cell cycle entry and G1 progression by CSF-1. Mol. Reprod. Dev., 46: 11–18, 1997.
83. Keshava, N., Gubba, S., and Tekmal, R. R. Overexpression of Macrophage Colony-stimulating Factor (CSF-1) and its Receptor, c-fms, in Normal Ovarian Granulosa Cells Leads to Cell Proliferation and Tumorigenesis. J. Soc. Gynecol. Investig., 6: 41–49, 1999.
84. Mishima, K., Higashiyama, S., Asai, A., Yamaoka, K., Nagashima, Y., Taniguchi, N., Kitanaka, C., Kirino, T., and Kuchino, Y. Heparin-binding Epidermal Growth Factor-like Growth Factor Stimulates Mitogenic Signaling and is Highly Expressed in Human Malignant Gliomas. Acta Neuropathologica, 96: 322–328, 1998.
85. Zhu, M. and Paddock, G. V. Expression of the Hepatocyte Growth Factor-like Protein Gene in Human Hepatocellular Carcinoma and Interleukin-6-induced Increased Expression in Hepatoma Cells. Biochim. Biophys. Acta, 1449: 63–72, 1999.
86. Wang, M. H., Dlugosz, A. A., Sun, Y., Suda, T., Skeel, A., and Leonard, E. J. Macrophage-stimulating protein induces proliferation and migration of murine keratinocytes. Exp. Cell Res., 226: 39–46, 1996.
87. Pelkey, T. J., Frierson, H. F., Mills, S. E., and Stoler, M. H. Detection of the alpha-subunit of Inhibin in Trophoblastic Neoplasia. Hum. Pathol., 30: 26–31, 1999.
88. Arola, J., Liu, J., Heikkila, P., Voutilainen, R., and Kahri, A. Expression of inhibin alpha in the human adrenal gland and adrenocortical tumors. Endocrine Res., 24: 865–867, 1998.
89. Kallakury, B. S., Sheehan, C. E., Rhee, S. J., Fisher, H. G., Kaufman, R. P. J., Rifkin, M. D., and Ross, J. S. The prognostic significance of proliferation-associated nucleolar protein p120 expression in prostate adenocarcinoma: A comparison with cyclins A and B1, Ki-67, proliferating cell nuclear antigen, and p34(cdc2). Cancer, 85: 1569–1576, 1999.

The contents of the publications and patents referenced herein are incorporated herein by reference in their entirety.

What is claimed is:

1. A method of inhibiting the proliferation of breast cancer cells in a patient in need of such inhibition, wherein said breast cancer cells are characterized by increased expression of peripheral-type benzodiazepine receptor protein, which comprises:
   determining whether said breast cancer cells exhibit elevated expression of peripheral-type benzodiazepine receptor protein, wherein said elevated expression is an at least 3-fold increase in the level of expression of peripheral-type benzodiazepine receptor protein as compared to normal cells; and
   administering an effective amount of isolated Ginkgolide B to said patient.

2. A method according to claim 1, wherein said proliferation of breast cancer cells is caused by the over-expression of oncogenes, and wherein the administering results in decreasing the expression of said oncogenes and combats the proliferation of said breast cancer cells.

3. A method according to claim 2, wherein said oncogenes are one or more of APC, PE-1, RhoA and c-Jun.

4. A method according to claim 1, wherein said administering results in decreasing the expression of peripheral-type benzodiazepine receptor in said breast cancer cells.

5. A method according to claim 4, wherein said breast cancer cells are human breast cancer cells.

6. A method according to claim 4, wherein the decreasing of the expression of peripheral-type benzodiazepine receptor is the result of decreasing the expression of peripheral-type benzodiazepine receptor mRNA in said breast cancer cells.

7. A method according to claim 1, wherein said administering results in increasing the expression of a c-Myc protooncogene.

8. A method according to claim 1, wherein said administering results in decreasing the expression of cell cycle regulators prothymosin-$\alpha$, CDK2, p55CDC, myeloblastin and p120 proliferating-cell nuclear antigen.

9. A method according to claim 1, wherein said administering results in decreasing the expression of intracellular signal transduction modulators NET1 and ERK2.

10. A method according to claim 1, wherein said administering results in decreasing the expression of apoptosis-related products Adenosine A2A Receptor, Flt3 ligand, Grb2, Clusterin, RXR-$\beta$, Glutathione S-transferase P, N-Myc, TRADD, SGP-2 and NIP-1.

11. A method according to claim 1, wherein said administering results in decreasing the expression of transcription factors Id-2, ATF-4, ETR101 and ETR-103.

12. A method according to claim 1, wherein said administering results in decreasing the expression of growth factors macrophage colony-stimulating factor-1, heparin-binding EGF-like growth factor, hepatocyte growth factor-like protein and inhibin $\alpha$.

13. A method according to claim 1, wherein said administering results in decreasing the expression of cell adhesion molecules CD19 B-lymphocyte antigen, L1CAM, $\beta$-catenin, integrin subunits $\alpha 3$, $\alpha 4$, $\alpha 6$, $\beta 5$, and $\alpha M$.

14. A method according to claim 1, wherein said administering results in decreasing the expression of genes APC, PE-1, RhoA, c-Jun, prothymosin-$\alpha$, CDK2, p55CDC, myeloblastin, p120 proliferating-cell nuclear antigen, NET1, ERK2, Adenosine A2A Receptor, Flt3 ligand, Grb2, Clusterin, RXR-$\beta$, Glutathione S-transferase P, N-Myc, TRADD, SGP-2, NIP-1, Id-2, ATF-4, ETR-101, ETR-103, macrophage colony-stimulating factor-1, heparin-binding EGF-like growth factor, hepatocyte growth factor-like protein, inhibin $\alpha$, CD19 B-lymphocyte antigen, L1CAM, $\beta$-catenin, and integrin subunits $\alpha 3$, $\alpha 4$, $\alpha 6$, $\beta 5$, and $\alpha M$.

* * * * *